United States Patent
Schoepgens et al.

(10) Patent No.: US 10,500,141 B2
(45) Date of Patent: *Dec. 10, 2019

(54) CREAM-TYPE HAIR COLORING AGENT II

(71) Applicant: Henkel AG & Co. KGaA, Duesseldorf (DE)

(72) Inventors: Juergen Schoepgens, Schwalmtal (DE); Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 61 days.

This patent is subject to a terminal disclaimer.

(21) Appl. No.: 15/826,697

(22) Filed: Nov. 30, 2017

(65) Prior Publication Data

US 2018/0168946 A1 Jun. 21, 2018

(30) Foreign Application Priority Data

Dec. 19, 2016 (DE) .................. 10 2016 225 377

(51) Int. Cl.
| | |
|---|---|
| *A61Q 5/10* | (2006.01) |
| *A61K 8/04* | (2006.01) |
| *A61K 8/19* | (2006.01) |
| *A61K 8/34* | (2006.01) |
| *A61K 8/81* | (2006.01) |
| *A61K 8/37* | (2006.01) |
| *A61K 8/86* | (2006.01) |

(52) U.S. Cl.
CPC ............ *A61K 8/042* (2013.01); *A61K 8/19* (2013.01); *A61K 8/342* (2013.01); *A61K 8/375* (2013.01); *A61K 8/8147* (2013.01); *A61K 8/8152* (2013.01); *A61K 8/8158* (2013.01); *A61K 8/86* (2013.01); *A61Q 5/10* (2013.01); *A61K 2800/4324* (2013.01); *A61K 2800/882* (2013.01)

(58) Field of Classification Search
CPC .. A61Q 5/10; A61K 8/342; A61K 2800/4324; A61K 2800/882; A61K 2800/884; A61K 8/345; A61K 8/375; A61K 8/042
See application file for complete search history.

(56) References Cited

U.S. PATENT DOCUMENTS

| | | | |
|---|---|---|---|
| 2002/0010970 A1* | 1/2002 | Cottard | A61K 8/342 8/405 |
| 2006/0277695 A1* | 12/2006 | Kleen | A61K 8/416 8/405 |
| 2008/0112898 A1 | 5/2008 | Schiemann | |
| 2012/0048288 A1* | 3/2012 | Reichert | A61K 8/442 132/208 |
| 2015/0352016 A1 | 12/2015 | Shah | |

FOREIGN PATENT DOCUMENTS

| | | |
|---|---|---|
| CN | 106619302 A | 5/2017 |
| WO | WO 2015/112787 A1 * | 7/2015 ............... A61Q 5/10 |

OTHER PUBLICATIONS

UKIPO Search Report in Application No. GB1719904.3 dated Aug. 15, 2018.
DIN 55672-3, "Gel Permeation Chromatography (GPC)—Part 3: Water as Eluent", Aug. 2007.

* cited by examiner

*Primary Examiner* — Eisa B Elhilo
(74) *Attorney, Agent, or Firm* — Lorenz & Kopf, LLP

(57) ABSTRACT

The subject of the present disclosure is agents for oxidative hair dyeing containing from about 65-about 83 wt. % water, oxidation dye precursor(s), alkalizing agent and a specific mixture of a crosslinked copolymer of acrylic acid and non-ethoxylated esters of acrylic acid with linear C10-C30-monoalcohols, glyceryl fatty acid esters, selected from fatty alcohol ethoxylated and linear, saturated C8-C22-alkan-1-ol, wherein the dye obtains the optimal viscosity for application and the consistency of a gel-like cream with outstanding haptics.

20 Claims, No Drawings

CREAM-TYPE HAIR COLORING AGENT II

CROSS-REFERENCE TO RELATED APPLICATION

This application claims priority to German Patent Application No. 10 2016 225 377.8, filed Dec. 19, 2016, which is incorporated herein by reference in its entirety.

TECHNICAL FIELD

The present disclosure relates to an oxidative hair coloring agent in cream form, a kit including this coloring agent and a hair coloring method using this coloring agent.

BACKGROUND

To achieve permanent, intense colors with corresponding fastness properties, so-called oxidative dyes are used. Said dyes usually contain oxidative dye precursors, so-called developer components and coupler components. The developer components join together or couple with one or more coupler components to form, under the influence of oxidants or atmospheric oxygen, the actual dyes per se. Indeed, the oxidative dyes are exemplified by outstanding, long-lasting color results. To achieve natural-looking colors, however, a mixture from a larger number of oxidative dye precursors (ODP) must normally be used; in many cases, partially-oxidizing dyes are still used to create the tinting effect.

Most of the oxidative dyes used for stabilizing the dye precursors during storage and to accelerate the reaction during oxidative application have an alkali pH value, which is set with alkalizing agents such as alkanolamines, ammonia or inorganic bases.

To produce the dye, the alkali coloring component is usually mixed with a hydrous hydrogen peroxide solution to form a homogeneous creme or a homogeneous gel, and then applied immediately to the hair to be dyed. This dye mixture remains on the hair for a period of 5 to 60 minutes, until the oxidative formation of the dye on the hair is complete. The dye mixture is then washed out.

The aforementioned oxidative precursors (OPC) and alkalizing agents are usually worked into the hair in a cosmetically suitable carrier, such as a creme, for example. The carrier guarantees a homogeneous distribution and an adequate dwell time of the hair dye on the hair.

BRIEF SUMMARY

Agents for oxidative hair dyeing, kits-of-parts including the agents, and methods for oxidative hair dyeing using the agent are provided herein. In an embodiment, an agent for oxidative hair dyeing includes water, at least one oxidation dye precursor, at least one alkalizing agent, at least one crosslinked copolymer including acrylic acid and non-ethoxylated esters of acrylic acid with linear C10-C30-monoalcohols as monomers, at least one linear, saturated 1-alkanol with a hydroxy group and from about 8 to about 22 carbon atoms, at least one glycerol fatty acid ester, at least one linear, saturated ethoxylated 1-alkanol with from about 8 to about 22 carbon atoms in the alkyl radical and degree of ethoxylation of from about 80 to about 120, at least one linear, saturated ethoxylated 1-alkanol with from about 8 to about 22 carbon atoms in the alkyl radical and degree of ethoxylation of from about 20 to about 50,. The at least one glycerol fatty acid ester has Formula (I)

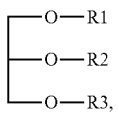

wherein R1, R2 and R3 denote a hydrogen atom or a methyl group independent of each other or a grouping of Formula (II),

wherein R4 denotes an unbranched or branched, saturated or unsaturated $C_{11}$-$C_{27}$-alkyl group, providing that at least one and a maximum of two of the radicals, selected from R1, R2, and R3, denotes a grouping of Formula (II). Relative to the weight of the agent in each case, the agent includes the water in an amount of from about 65 -about 83 wt. %, the cross-linked copolymer in a total quantity of from about 0.1 -about 0.8 wt. %, the at least one linear, saturated 1-alkanol with a hydroxy group and from about 8 to about 22 carbon atoms in a total amount of from about 3-about 7 wt. %, the at least one glycerol fatty acid ester in a total amount of from about 0.2 -about 2 wt. %, the at least one linear, saturated ethoxylated 1-alkanol with from about 8 to about 22 carbon atoms in the alkyl radical and degree of ethoxylation of from about 80 to about 120 in a total amount of from about 0.1-about 2 wt. %, and the at least one linear, saturated ethoxylated 1-alkanol with from about 8 to about 22 carbon atoms in the alkyl radical and degree of ethoxylation of from about 20 to about 50 in a total amount of from about 0.1-about 2 wt. %. The agent does not contain any oxidants.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The task of the present disclosure was to prepare an oxidative hair-coloring agent that has a cream-like consistency, haptics and appearance with a consistently high viscosity by reducing the content of melting, grease components which have a thickening effect.

Said problems are solved by an agent for oxidative hair dye containing the following, in each case relative to its weight:

- from about 65 -about 83 wt. % water,
- at least one oxidation dye precursor,
- at least one alkalizing agent,
- at least one crosslinked copolymer including acrylic acid and non-ethoxylated esters of acrylic acid with linear C10-C30 monoalcohols as monomers, wherein the crosslinked copolymer is contained in a total amount of from about 0.1-about 0.8 wt. %, preferably from about 0.1-about 0.6 wt. %, particularly from about 0.2-about 0.5 wt. %, relative to the weight of the agent in each case,
- at least one linear, saturated 1-alkanol with a hydroxy group and from about 8 to about 22 carbon atoms in a total amount of from about 3-about 7 wt. %, preferably from about 4-about 6 wt. %, particularly from about 4.5-about 5.5 wt. %, in a total amount of from about 0.2-about 2 wt. %, preferably from about 0.3-about 1.5 wt. %, particularly from about 0.4-about 0.8 wt. %, at least one glyceryl fatty acid ester having the formula (I)

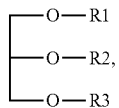
(I)

wherein

R1, R2 and R3 denote a hydrogen atom or a methyl group independent of each other or a grouping of Formula (II),

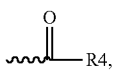
(II)

wherein

R4 denotes an unbranched or branched, saturated or unsaturated $C_{11}$-$C_{27}$-alkyl group, providing that at least one and a maximum of two of the radicals, selected from R1, R2, and R3, denotes a grouping of Formula (II);

at least one linear, saturated ethoxylated 1-alkanol with from about 8 to about 22 carbon atoms in the alkyl radical and degree of ethoxylation of from about 80 to about 120 in a total amount of from about 0.1-about 2 wt. %, preferably from about 0.2-about 1.5 wt. %, particularly from about 0.4-about 1 wt. % and at least one linear, saturated ethoxylated 1-alkanol with from about 8 to about 22 carbon atoms in the alkyl radical and degree of ethoxylation of from about 20 to about 50, preferably from about 30-about 35, in a total amount of from about 0.1-about 2 wt. %, preferably from about 0.2-about 1.5 wt. %, particularly from about 0.4-about 1 wt. %, wherein no oxidants are contained.

The agent as contemplated herein constitutes the alkali dye component of an oxidative hair dye. This is usually mixed immediately before application with a hydrous hydrogen peroxide preparation and then applied to the hair to be dyed. Until mixed with the hydrous hydrogen peroxide preparation, the agent as contemplated herein contains no oxidants.

The agent as contemplated herein contains, in each case relative to its weight, from about 65-about 83 wt. % water, preferably from about 70-about 80 wt. %, particularly from about 73-about 78 wt. % water.

Alkalizing Agent

The agent as contemplated herein contains at least one alkalizing agent. The alkalizing agent preferred as contemplated herein for setting the preferred pH value is selected from the group comprising ammonium hydroxide, basic amino acids, alkali hydroxides, alkanolamines, alkali metal meta silicates, alkali phosphates and alkali hydrogen phosphates, as well as the mixtures thereof. Lithium, sodium and potassium, particularly sodium or potassium are preferred for use as alkali metal ions.

The basic amino acids that can be used as alkalizing agents are preferably selected from the group of L-arginine, D-arginine, D,L-arginine, L-lysine, D-lysine, D,L-lysine, L-arginine, D-arginine, D,L-arginine, are more preferably used as alkalizing agents as contemplated herein.

The alkali hydroxides that can be used as alkalizing agents are preferably selected from sodium hydroxide and potassium hydroxide.

The alkanolamines usable as alkalization agents are preferably selected from primary amines with a $C_2$-$C_6$-alkyl base body having at least one hydroxyl group. More preferred alkanolamines are selected from the group comprising 2-aminoethan-1-ol (monoethanolamine), 3-aminopropan-1-ol, 4-amino-butan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. Most preferred alkanolamines as contemplated herein are selected from the group of 2-aminoethan-1-ol, 2-amino-2-methylpropan-1-ol and 2-amino-2-methyl-propan-1,3-diol.

A most preferred alkalizing agent as contemplated herein is monoethanolamine (2-aminoethan-1-ol). To achieve the most odorless dye method possible and to optimize the color fastness properties of the dye, monoethanolamine is contained in a total quantity of from about 0.2-about 10 wt. %, preferably from about 0.5-about 8 wt. %, more preferably from about 1 to about 6 wt. % and most preferably from about 2 to about 4 wt. %—relative to the weight of the dye as contemplated herein.

In addition to and/or instead of monoethanolamine, other preferred dyes as contemplated herein are ammonium hydroxide, i.e. ammonia in the form of its hydrous solution. Suitable hydrous ammonia solutions are from about 10 to about 35 percentage solutions (calculated in vol. %.) 100 g of hydrous ammonia solution with 25 vol. % $NH_3$ contain approx. 50 g of ammonia. Ammonia is preferably used in the form of a from about 20 to about 30 vol. % solution, most preferably in the form of a 25 vol. % solution.

In a most preferred embodiment, the dye as contemplated herein contains ammonium hydroxide in a quantity of from about 0.2 to about 6 wt. %, preferably from about 0.3 to about 5 wt. %, more preferably from about 0.5 to about 3 wt. % and most preferably from about 1 to about 2 wt. %, relative to the weight of the dye as contemplated herein.

Other alkalizing agents such as potassium hydroxide and sodium hydroxide can also be contained, preferably in a total quantity of from about 0.05 to about 1.5 wt. %, most preferably from about 0.1 to about 0.6 wt. %, in each case relative to the weight of the dye as contemplated herein.

In another most preferred embodiment, the dye as contemplated herein contains at least one alkalizing agent in a total quantity of from about 0.02-about 0.4 mol/100 g, preferably from about 0.05-about 0.3 mol/100 g, in each case in mol of alkalizing agents per 100 grams of agent as contemplated herein.

Preferred agents as contemplated herein are exemplified by a pH value in the range of from about 8-about 12, preferably from about 9-about 11.5, more preferably from about 9.5-about 10.5, in each case measured at 20° C.

A further essential feature of the agent of the present disclosure is the content of at least one crosslinked copolymer including acrylic acid and non-ethoxylated esters of acrylic acid with linear C10-C30 monoalcohols as monomers, wherein the crosslinked copolymer is contained in a total amount of from about 0.1-about 0.8 wt. %, preferably from about 0.1-about 0.6 wt. %, particularly from about 0.2-about 0.5 wt. %, relative to the weight of the agent in each case. The at least one cross-linked copolymer from acrylic acid and non-ethoxylated esters of acrylic acid having linear C10-C30 mono-alcohols is preferably selected from copolymers having the INCI trade name of Acrylates/C10-30 Alkyl Acrylate Crosspolymer. Sucrose allyl ether or pentaerythrityl allyl ether is preferably contained as the cross-linking agent.

Cross-linked copolymers from acrylic acid and non-ethoxylated esters of acrylic acid having linear C10-C30 mono-alcohols, which are most preferred as contemplated herein, can be obtained by polymerizing a monomer mixture which—in each case relative to its weight—contains from about 80 to about 99 wt. %, preferably from about 90 to about 98 wt. %, acrylic acid, at least one non-ethoxylated ester of acrylic acid having linear C10-C30 mono-alcohols in a total quantity of from about 0.9-about 19.9 wt. %, preferably from about 2-about 10 wt. %, as well as a cross-linking agent in a total quantity of from about 0.1-about 4 wt. %.

Other cross-linked copolymers from acrylic acid and non-ethoxylated esters having linear C10-C30 mono-alcohols, which are most preferred as contemplated herein, are exemplified in that their 0.5 wt. % dispersion in water at 25° C. and a pH value in the range of from about 5.8-about 6.3 has a viscosity in the range of from about 45,000 to about 65,000 mPas, measured by employing a Brookfield RVF or a Brookfield RVT viscometer at a rotational frequency of 20 rpm with Spindle #7.

The content of the at least one cross-linked copolymer, constructed from acrylic acid and non-ethoxylated esters with acrylic acid having linear C10-C30 mono-alcohols as monomers, is preferably selected such that the viscosity of the agent as contemplated herein is within the range of from about 20,000-about 90,000 mPas, preferably from about 25,000-about 65,000 mPas, particularly from about 30,000-about 35,000 mPas, in each case measured at 22° C. by employing a Brookfield rotational viscometer at a rotational frequency of 4 rpm with Spindle TC.

Furthermore, the agents of the present disclosure and agents used as contemplated herein contain at least one linear, saturated 1-alkanol with a hydroxy group and from about 8 to about 22 carbon atoms in a total amount of from about 3-about 7 wt. %, preferably from about 4-about 6 wt. %, particularly from about 4.5-about 5.5 wt. %, relative to the weight of the agent in each case. As contemplated herein, it is preferable that at least one linear, saturated 1-alkanol with a hydroxy group and from about 8 to about 22 carbon atoms selected from 1-decanol, 1-dodecanol (lauryl alcohol), 1-tridecanol, 1-tetradecanol (myristylalcohol), 1-hexadecanol (cetyl alcohol), 1-octadecanol (stearyl alcohol) and 1-eicosanol (arachyl alcohol), as well as mixtures thereof. A preferred alkanol mixture as contemplated herein is coconut alcohol, i.e. alkanol mixtures that are obtained by employing hydrogenation of coconut oil. Particularly preferred coconut alcohol as contemplated herein has the following chain length distribution, relative to its weight in each case: C10 and shorter: zero to 3 wt. %, C12: from about 48-about 58 wt. %, C14: from about 18-about 24 wt. %, C16: from about 8-about 12 wt. %, C18: from about 11-about 15 wt. %, C20: zero to 1 wt. %. Particularly preferred C8-C22-alkan-1-ols as contemplated herein are selected from 1-tetradecanol (myristyl alcohol), cetyl alcohol and stearyl alcohol, and mixtures thereof, in particular mixtures of cetyl alcohol and stearyl alcohol.

Furthermore, the agents of the present disclosure and agents used as contemplated herein contain, in a total amount of from about 0.2-about 2 wt. %, preferably from about 0.3-about 1.5 wt. %, particularly from about 0.4-about 0.8 wt. %, at least one glyceryl fatty acid ester having the formula (I)

wherein
R1, R2 and R3 denote a hydrogen atom or a methyl group independent of each other or a grouping of Formula (II),

wherein
R4 denotes an unbranched or branched, saturated or unsaturated $C_{11}$-$C_{27}$-alkyl group,
providing that at least one and a maximum of two of the radicals, selected from R1, R2, and R3, denotes a grouping of Formula (II).

The radical R4 in Formula (II) denotes an unbranched or branched, saturated or unsaturated $C_{11}$-$C_{27}$-alkyl group.

R4 preferably denotes an unbranched, saturated $C_{11}$-$C_{27}$-alkyl group. R4 more preferably denotes an unbranched, saturated $C_{13}$-$C_{23}$-alkyl group. R4 denotes, in particular, an unbranched, saturated $C_{15}$-$C_{17}$-alkyl.

In a further preferred embodiment, an agent as contemplated herein contains at least one compound from the group of formulae (Ia) to (Id) as a glyceryl fatty acid ester having the formula (I).

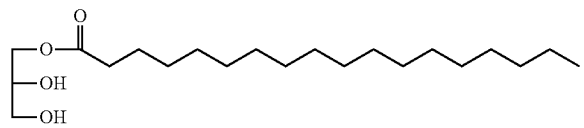

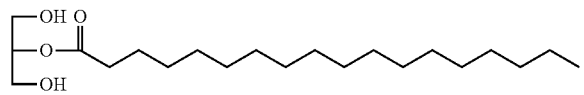

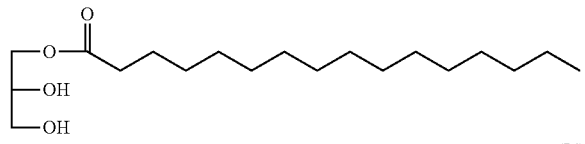

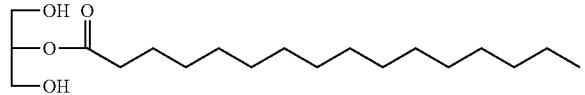

Compounds of formula (Ia) to (Id) are also known by the names Glyceryl monostearate and glyceryl monopalmitate.

In a further preferred embodiment, an agent as contemplated herein contains at least one compound from the group of formulae (Ie) to (Ih) as a glyceryl fatty acid ester having the formula (I):

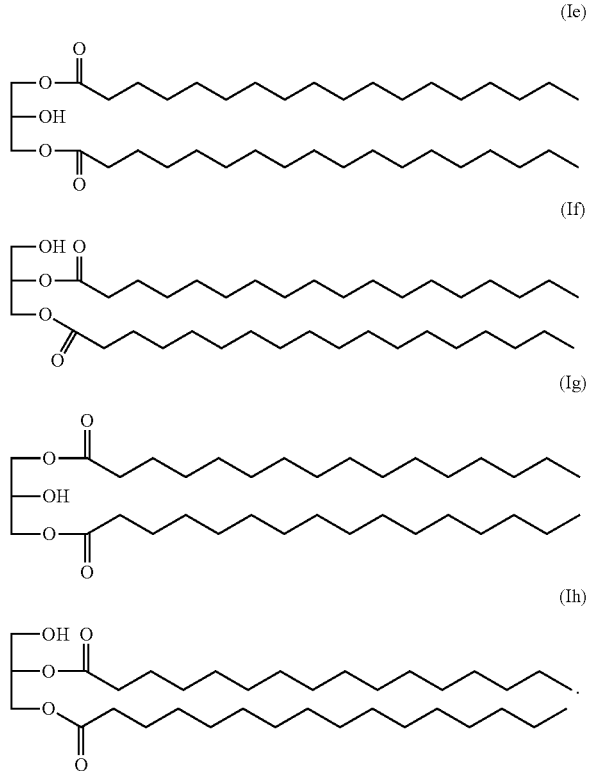

Compounds of formula (Ie) to (Ih) are also known by the names Glyceryl distearate and glyceryl dipalmitate.

In a particularly preferred embodiment, agents as contemplated herein are exemplified in that they contain at least one compound from the group of formulae (Ia) to (Ih) as a glyceryl fatty acid ester having the formula (I). In a further preferred embodiment, an agent as contemplated herein contains at least one compound glyceryl monostearate, glyceryl distearate, glyceryl monopalmitate and glyceryl dipalmitate as a glyceryl fatty acid ester having the formula (I).

Furthermore, the agents of the present disclosure and agents used as contemplated herein contain at least one linear, saturated ethoxylated 1-alkanol with from about 8 to about 22 carbon atoms in the alkyl radical and degree of ethoxylation of from about 80 to about 120 in a total amount of from about 0.1-about 2 wt. %, preferably from about 0.2-about 1.5 wt. %, particularly from about 0.4-about 1 wt. %, relative to the weight of the agent in each case.

Preferred linear, saturated 1-alkanols with from about 8 to about 22 carbon atoms, which are the essential component of the ethoxylated 1-alkanols with an ethoxylation degree of from about 80 to about 120 for the present disclosure, are selected from octan-1-ol (octyl alcohol, capryl alcohol), decan-1-ol (decyl alcohol, caprin alcohol), dodecan-1-ol (dodecyl alcohol, lauryl alcohol), tetradecan-1-ol, (tetradecyl alcohol, myristyl alcohol), hexadecan-1-ol (hexadecyl alcohol, cetyl alcohol, palmityl alcohol), cctadecan-1-ol (octadecyl alcohol, stearyl alcohol), eicosan-1-ol (eicosyl alcohol, arachyl alcohol) and cocosan-1-ol (docosyl alcohol, behenyl alcohol). Within this group, hexadecan-1-ol (hexadecyl alcohol, cetyl alcohol, palmityl alcohol) and octadecan-1-ol (octadecyl alcohol, stearyl alcohol) are particularly preferred 1-alcanols.

Ethoxylation (also oxyethoxylation) is understood to mean the reaction of fatty alcohols with ethylene oxide (EO). With insertion of from about 80 to about 120 groupings of the type —CH2-CH2-O— per fatty alcohol module, linear polyethers having a hydroxy group on one chain end and the $C_8$-$C_{22}$-alkyl group of fatty alcohol on the other chain end are obtained.

Preferred ethoxylated 1-alkanols of this type have a degree of ethoxylation of from about 90 to about 110. Particular preference is given to use of linear, saturated ethoxylated 1-alkanols that have an ethoxylation degree of 100.

In the course of the work leading to this present disclosure, it was found that the ethoxylation degree of the highly ethoxylated (from about 80-about 120 EO) 1-alkanol in interaction with the at least one ethoxylated (from about 20 to about 50, preferably from about 30-about 35 EO) 1-alkanol agent indicated below had a surprising influence on the thickening properties and consistency of the agent. For this reason, particular preference is given to use of one or multiple linear, saturated ethoxylated 1-alkanols having a very specific degree of ethoxylation.

A particularly advantageous and thus explicitly preferred agent for dyeing keratinous fibres contains, as a linear, saturated ethoxylated 1-alkanol with from about 8 to about 22 carbon atoms in the alkyl radical and an ethoxylation degree of from about 80 to about 120 in a total amount of from about 0.1-about 2 wt. %, preferably from about 0.2-about 1.5 wt. %, particularly from about 0.4-about 1 wt. %, relative to the weight of the agent in each case, one or multiple compounds of the group hexadecan-1-ol (hexadecyl alcohol, cetyl alcohol, palmityl alcohol), ethoxylated with 90 EO,
hexadecan-1-ol (hexadecyl alcohol, cetyl alcohol, palmityl alcohol), ethoxylated with 91 EO,
hexadecan-1-ol (hexadecyl alcohol, cetyl alcohol, palmityl alcohol), ethoxylated with 92 EO,
hexadecan-1-ol (hexadecyl alcohol, cetyl alcohol, palmityl alcohol), ethoxylated with 93 EO,
hexadecan-1-ol (hexadecyl alcohol, cetyl alcohol, palmityl alcohol), ethoxylated with 94 EO,
hexadecan-1-ol (hexadecyl alcohol, cetyl alcohol, palmityl alcohol), ethoxylated with 95 EO,
hexadecan-1-ol (hexadecyl alcohol, cetyl alcohol, palmityl alcohol), ethoxylated with 96 EO,
hexadecan-1-ol (hexadecyl alcohol, cetyl alcohol, palmityl alcohol), ethoxylated with 97 EO,
hexadecan-1-ol (hexadecyl alcohol, cetyl alcohol, palmityl alcohol), ethoxylated with 98 EO,
hexadecan-1-ol (hexadecyl alcohol, cetyl alcohol, palmityl alcohol), ethoxylated with 99 EO,
hexadecan-1-ol (hexadecyl alcohol, cetyl alcohol, palmityl alcohol), ethoxylated with 100 EO,
hexadecan-1-ol (hexadecyl alcohol, cetyl alcohol, palmityl alcohol), ethoxylated with 101 EO,
hexadecan-1-ol (hexadecyl alcohol, cetyl alcohol, palmityl alcohol), ethoxylated with 102 EO,
hexadecan-1-ol (hexadecyl alcohol, cetyl alcohol, palmityl alcohol), ethoxylated with 103 EO,
hexadecan-1-ol (hexadecyl alcohol, cetyl alcohol, palmityl alcohol), ethoxylated with 104 EO,
hexadecan-1-ol (hexadecyl alcohol, cetyl alcohol, palmityl alcohol), ethoxylated with 105 EO, hexadecan-1-ol (hexadecyl alcohol, cetyl alcohol, palmityl alcohol), ethoxylated with 106 EO,
hexadecan-1-ol (hexadecyl alcohol, cetyl alcohol, palmityl alcohol), ethoxylated with 107 EO,
hexadecan-1-ol (hexadecyl alcohol, cetyl alcohol, palmityl alcohol), ethoxylated with 108 EO,
hexadecan-1-ol (hexadecyl alcohol, cetyl alcohol, palmityl alcohol), ethoxylated with 109 EO,
hexadecan-1-ol (hexadecyl alcohol, cetyl alcohol, palmityl alcohol), ethoxylated with 110 EO,
octadecan-1-ol (octadecyl alcohol, stearyl alcohol), ethoxylated with 90 EO,
octadecan-1-ol (octadecyl alcohol, stearyl alcohol), ethoxylated with 91 EO,
octadecan-1-ol (octadecyl alcohol, stearyl alcohol), ethoxylated with 92 EO,
octadecan-1-ol (octadecyl alcohol, stearyl alcohol), ethoxylated with 93 EO,
octadecan-1-ol (octadecyl alcohol, stearyl alcohol), ethoxylated with 94 EO,
octadecan-1-ol (octadecyl alcohol, stearyl alcohol), ethoxylated with 95 EO,
octadecan-1-ol (octadecyl alcohol, stearyl alcohol), ethoxylated with 96 EO,
octadecan-1-ol (octadecyl alcohol, stearyl alcohol), ethoxylated with 97 EO,
octadecan-1-ol (octadecyl alcohol, stearyl alcohol), ethoxylated with 98 EO,
octadecan-1-ol (octadecyl alcohol, stearyl alcohol), ethoxylated with 99 EO,
octadecan-1-ol (octadecyl alcohol, stearyl alcohol), ethoxylated with 100 EO,
octadecan-1-ol (octadecyl alcohol, stearyl alcohol), ethoxylated with 101 EO,
octadecan-1-ol (octadecyl alcohol, stearyl alcohol), ethoxylated with 102 EO,
octadecan-1-ol (octadecyl alcohol, stearyl alcohol), ethoxylated with 103 EO,
octadecan-1-ol (octadecyl alcohol, stearyl alcohol), ethoxylated with 104 EO,
octadecan-1-ol (octadecyl alcohol, stearyl alcohol), ethoxylated with 105 EO,
octadecan-1-ol (octadecyl alcohol, stearyl alcohol), ethoxylated with 106 EO,
octadecan-1-ol (octadecyl alcohol, stearyl alcohol), ethoxylated with 107 EO,
octadecan-1-ol (octadecyl alcohol, stearyl alcohol), ethoxylated with 108 EO,
octadecan-1-ol (octadecyl alcohol, stearyl alcohol), ethoxylated with 109 EO,
octadecan-1-ol (octadecyl alcohol, stearyl alcohol), ethoxylated with 110 EO, Particular preference is given to Steareth-100. Particular preference is given to inventive agents and agents used as contemplated herein containing from about 0.1-about 2 wt. %, preferably from about 0.2-about 1.5 wt. %, particularly from about 0.4-about 1 wt. % Steareth-100, relative to the weight of the agent in each case.

Furthermore, the agents of the present disclosure and agents used as contemplated herein contain at least one linear, saturated ethoxylated 1-alkanol with from about 8 to about 22 carbon atoms in the alkyl radical and degree of ethoxylation of from about 20 to about 50, preferably from about 30-about 35, in a total amount of from about 0.1-about 2 wt. %, preferably from about 0.2-about 1.5 wt. %, particularly from about 0.4-about 1 wt. %, relative to the weight of the agent in each case.

Preferred linear, saturated 1-alkanols with from about 8 to about 22 carbon atoms, which are the essential component of the ethoxylated 1-alkanols with an ethoxylation degree of from about 20 to about 50, preferably from about 30-about 35, for the present disclosure, are selected from octan-1-ol (octyl alcohol, capryl alcohol), decan-1-ol (decyl alcohol, caprin alcohol), dodecan-1-ol (dodecyl alcohol, lauryl alcohol), tetradecan-1-ol, (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), eicosan-1-ol (eicosyl alcohol, arachyl alcohol) and cocosan-1-ol (docosyl alcohol, behenyl alcohol). Within this group, hexadecan-1-ol and octadecan-1-ol are particularly preferred 1-alcanols.

In the course of the work leading to this present disclosure, it was found that the ethoxylation degree of the moderately ethoxylated (from about 20 to about 50, preferably from about 30-about 35 EO) 1-alkanol in interaction with the at least one highly ethoxylated (from about 80-about 120 EO) 1-alkanol agent indicated below had a surprising influence on the thickening properties and consistency of the agent. For this reason, particular preference is given to use of one or multiple linear, saturated ethoxylated 1-alkanols having a very specific degree of ethoxylation.

A particularly advantageous and thus explicitly preferred agent for dyeing keratinous fibres contains, as a linear, saturated ethoxylated 1-alkanol with from about 8 to about 22 carbon atoms in the alkyl radical and an ethoxylation degree of from about 20 to about 50, preferably from about 30-about 35, in a total amount of from about 0.1-about 2 wt. %, preferably from about 0.2-about 1.5 wt. %, particularly from about 0.4-about 1 wt. %, relative to the weight of the agent in each case, one or multiple compounds of the group
hexadecan-1-ol (hexadecyl alcohol, cetyl alcohol, palmityl alcohol), ethoxylated with 20 EO,
hexadecan-1-ol (hexadecyl alcohol, cetyl alcohol, palmityl alcohol), ethoxylated with 21 EO,
hexadecan-1-ol (hexadecyl alcohol, cetyl alcohol, palmityl alcohol), ethoxylated with 22 EO,
hexadecan-1-ol (hexadecyl alcohol, cetyl alcohol, palmityl alcohol), ethoxylated with 23 EO,
hexadecan-1-ol (hexadecyl alcohol, cetyl alcohol, palmityl alcohol), ethoxylated with 24 EO,
hexadecan-1-ol (hexadecyl alcohol, cetyl alcohol, palmityl alcohol), ethoxylated with 25 EO,
hexadecan-1-ol (hexadecyl alcohol, cetyl alcohol, palmityl alcohol), ethoxylated with 26 EO,
hexadecan-1-ol (hexadecyl alcohol, cetyl alcohol, palmityl alcohol), ethoxylated with 27 EO,
hexadecan-1-ol (hexadecyl alcohol, cetyl alcohol, palmityl alcohol), ethoxylated with 28 EO,
hexadecan-1-ol (hexadecyl alcohol, cetyl alcohol, palmityl alcohol), ethoxylated with 29 EO,
hexadecan-1-ol (hexadecyl alcohol, cetyl alcohol, palmityl alcohol), ethoxylated with 30 EO,
hexadecan-1-ol (hexadecyl alcohol, cetyl alcohol, palmityl alcohol), ethoxylated with 31 EO,
hexadecan-1-ol (hexadecyl alcohol, cetyl alcohol, palmityl alcohol), ethoxylated with 32 EO,
hexadecan-1-ol (hexadecyl alcohol, cetyl alcohol, palmityl alcohol), ethoxylated with 33 EO,
hexadecan-1-ol (hexadecyl alcohol, cetyl alcohol, palmityl alcohol), ethoxylated with 34 EO,
hexadecan-1-ol (hexadecyl alcohol, cetyl alcohol, palmityl alcohol), ethoxylated with 35 EO, hexadecan-1-ol (hexadecyl alcohol, cetyl alcohol, palmityl alcohol), ethoxylated with 36 EO,
hexadecan-1-ol (hexadecyl alcohol, cetyl alcohol, palmityl alcohol), ethoxylated with 37 EO,
hexadecan-1-ol (hexadecyl alcohol, cetyl alcohol, palmityl alcohol), ethoxylated with 38 EO,
hexadecan-1-ol (hexadecyl alcohol, cetyl alcohol, palmityl alcohol), ethoxylated with 39 EO,
hexadecan-1-ol (hexadecyl alcohol, cetyl alcohol, palmityl alcohol), ethoxylated with 40 EO,
hexadecan-1-ol (hexadecyl alcohol, cetyl alcohol, palmityl alcohol), ethoxylated with 41 EO,
hexadecan-1-ol (hexadecyl alcohol, cetyl alcohol, palmityl alcohol), ethoxylated with 42 EO,
hexadecan-1-ol (hexadecyl alcohol, cetyl alcohol, palmityl alcohol), ethoxylated with 43 EO,
hexadecan-1-ol (hexadecyl alcohol, cetyl alcohol, palmityl alcohol), ethoxylated with 44 EO,
hexadecan-1-ol (hexadecyl alcohol, cetyl alcohol, palmityl alcohol), ethoxylated with 45 EO,
hexadecan-1-ol (hexadecyl alcohol, cetyl alcohol, palmityl alcohol), ethoxylated with 46 EO,
hexadecan-1-ol (hexadecyl alcohol, cetyl alcohol, palmityl alcohol), ethoxylated with 47 EO,
hexadecan-1-ol (hexadecyl alcohol, cetyl alcohol, palmityl alcohol), ethoxylated with 48 EO,
hexadecan-1-ol (hexadecyl alcohol, cetyl alcohol, palmityl alcohol), ethoxylated with 49 EO,
hexadecan-1-ol (hexadecyl alcohol, cetyl alcohol, palmityl alcohol), ethoxylated with 50 EO,
octadecan-1-ol (octadecyl alcohol, stearyl alcohol), ethoxylated with 20 EO,
octadecan-1-ol (octadecyl alcohol, stearyl alcohol), ethoxylated with 21 EO,
octadecan-1-ol (octadecyl alcohol, stearyl alcohol), ethoxylated with 22 EO,
octadecan-1-ol (octadecyl alcohol, stearyl alcohol), ethoxylated with 23 EO,
octadecan-1-ol (octadecyl alcohol, stearyl alcohol), ethoxylated with 24 EO,
octadecan-1-ol (octadecyl alcohol, stearyl alcohol), ethoxylated with 25 EO,
octadecan-1-ol (octadecyl alcohol, stearyl alcohol), ethoxylated with 26 EO,
octadecan-1-ol (octadecyl alcohol, stearyl alcohol), ethoxylated with 27 EO,
octadecan-1-ol (octadecyl alcohol, stearyl alcohol), ethoxylated with 28 EO,
octadecan-1-ol (octadecyl alcohol, stearyl alcohol), ethoxylated with 29 EO,
octadecan-1-ol (octadecyl alcohol, stearyl alcohol), ethoxylated with 30 EO,
octadecan-1-ol (octadecyl alcohol, stearyl alcohol), ethoxylated with 31 EO,
octadecan-1-ol (octadecyl alcohol, stearyl alcohol), ethoxylated with 32 EO,
octadecan-1-ol (octadecyl alcohol, stearyl alcohol), ethoxylated with 33 EO,
octadecan-1-ol (octadecyl alcohol, stearyl alcohol), ethoxylated with 34 EO,
octadecan-1-ol (octadecyl alcohol, stearyl alcohol), ethoxylated with 35 EO,
octadecan-1-ol (octadecyl alcohol, stearyl alcohol), ethoxylated with 36 EO,
octadecan-1-ol (octadecyl alcohol, stearyl alcohol), ethoxylated with 37 EO,
octadecan-1-ol (octadecyl alcohol, stearyl alcohol), ethoxylated with 38 EO,
octadecan-1-ol (octadecyl alcohol, stearyl alcohol), ethoxylated with 39 EO,
octadecan-1-ol (octadecyl alcohol, stearyl alcohol), ethoxylated with 40 EO,
octadecan-1-ol (octadecyl alcohol, stearyl alcohol), ethoxylated with 41 EO,
octadecan-1-ol (octadecyl alcohol, stearyl alcohol), ethoxylated with 42 EO,
octadecan-1-ol (octadecyl alcohol, stearyl alcohol), ethoxylated with 43 EO,
octadecan-1-ol (octadecyl alcohol, stearyl alcohol), ethoxylated with 44 EO,
octadecan-1-ol (octadecyl alcohol, stearyl alcohol), ethoxylated with 45 EO,
octadecan-1-ol (octadecyl alcohol, stearyl alcohol), ethoxylated with 46 EO,
octadecan-1-ol (octadecyl alcohol, stearyl alcohol), ethoxylated with 47 EO,
octadecan-1-ol (octadecyl alcohol, stearyl alcohol), ethoxylated with 48 EO,
octadecan-1-ol (octadecyl alcohol, stearyl alcohol), ethoxylated with 49 EO,
octadecan-1-ol (octadecyl alcohol, stearyl alcohol), ethoxylated with 50 EO.

Particular preference is given to saturated ethoxylated 1-alkanols with from about 8 to about 22 carbon atoms in the alkyl radical and an ethoxylation degree of from about 20 to about 50 selected from Ceteth-20, Ceteth-25, Ceteth-30, Ceteth-35, Ceteth-40, Ceteth-45, Ceteth-50, Steareth-20, Steareth-25, Steareth-30, Steareth-35, Steareth-40, Steareth-45, Steareth-50, Ceteareth-20, Ceteareth-25, Ceteareth-30, Ceteareth-35, Ceteareth-40, Ceteareth-45, Ceteareth-50 and mixtures thereof.

Particular preference is given to agents of the present disclosure and agents used as contemplated herein containing, in a total amount of from about 0.1-about 2 wt. %, preferably from about 0.2-about 1.5 wt. %, particularly from about 0.4-about 1 wt. %, relative to the weight of the agent in each case, at least one compound selected from Ceteth-20, Ceteth-25, Ceteth-30, Ceteth-35, Ceteth-40, Ceteth-45, Ceteth-50, Steareth-20, Steareth-25, Steareth-30, Steareth-35, Steareth-40, Steareth-45, Steareth-50, Ceteareth-20, Ceteareth-25, Ceteareth-30, Ceteareth-35, Ceteareth-40, Ceteareth-45, Ceteareth-50 and mixtures thereof.

Even greater preference is given to agents of the present disclosure and agents used as contemplated herein containing, from about 0.1-about 2 wt. %, preferably from about 0.2-about 1.5 wt. %, particularly from about 0.4-about 1 wt. Steareth-100 and in a total amount of from about 0.1-about 2 wt. %, preferably from about 0.2-about 1.5 wt. %, particularly from about 0.4-about 1 wt. %, relative to the weight of the agent in each case, at least one compound selected from Ceteth-20, Ceteth-25, Ceteth-30, Ceteth-35, Ceteth-40, Ceteth-45, Ceteth-50, Steareth-20, Steareth-25, Steareth-30, Steareth-35, Steareth-40, Steareth-45, Steareth-50, Ceteareth-20, Ceteareth-25, Ceteareth-30, Ceteareth-35, Ceteareth-40, Ceteareth-45, Ceteareth-50 and mixtures thereof.

Additional particularly preferred agents and agents used as contemplated herein are exemplified in that the weight ratio of the total amount of linear, saturated ethoxylated 1-alkanols with from about 8 to about 22 carbon atoms in the alkyl radical and an ethoxylation degree of from about 20 to about 50 to the total amount of linear, saturated ethoxylated 1-alkanols with from about 8 to about 22 carbon atoms in the alkyl radical and an ethoxylation degree of from about 80 to about 120 is in the range of from about 1.5-about 2.5, preferably 2.

The combination of the crosslinked copolymers of acrylic acid and non-ethoxylated esters of acrylic acid having linear C10-C30 monoalcohols, linear, saturated 1-alkanol, glyceryl fatty acid esters of formula (I), highly ethoxylated 1-alkanols (from about 80-about 120 EO) and moderately ethoxylated 1-alkanols (from about 20-about 50 EO) achieves an especially rich, creamy consistency and haptics of the dye cream as contemplated herein and preferred as contemplated herein.

Additional preferred agents or agents used as contemplated herein are exemplified in that at least one linear saturated alcohol with two or three hydroxy groups and from about 2 to about 8 carbon atoms in the alkyl group, which is preferably selected from 1,2-propanediol and glycerin, as well as mixtures thereof is contained in a total amount of from about 0.5-about 15 wt. %, preferably from about 1-about 10 wt. %, particularly from about 2-about 8 wt. %. The addition of these linear saturated alkanols with two or three hydroxy groups and from about 2 to about 8 carbon atoms, particularly the addition of 1,2-propanediol and/or glycerin achieves further improvement of the cream-gel structure.

Other preferred agents of the present disclosure or agents used as contemplated herein are exemplified in that they contain at least one polymer selected from cationic and zwitterionic polymers in a total amount of from about 0.1-about 2 wt. %, preferably from about 0.2-about 1.5 wt. %, particularly from about 0.4-about 1 wt. %, relative to the weight of the agent in each case.

Surprisingly, it was found that the addition of a cationic and zwitterionic polymer in a total amount of from about 0.1-about 2 wt. % further improves the cream gel structure.

The term polymers is understood to mean macromolecules having a molecular weight of at least about 1000 g/mol, preferably at least about 2500 g/mol, particularly at least about 5000 g/mol, which includes the same, repeating organic units. Polymers are produced by polymerization of a monomer type or by polymerization of different, structurally different monomer types. If the polymer is produced by polymerization of a monomer type, it is referred to as a homopolymer. If structurally different monomer types are used in the polymerization, they are referred to as copolymers by a person skilled in the art.

The maximum molecular weight of the polymer depends on the degree of polymerization (number of polymerized monomers) and is partly determined by the polymerization method. Within the context of the present disclosure, it is preferred that the molecular weight of the zwitterionic polymer is from about 100,000 to about $10^7$ g/mol, preferably from about 200,000 to about $5 \cdot 10^6$ g/mol and particularly from about 500,000 to about $1 \cdot 10^6$ g/mol.

Zwitterionic polymers are understood to mean polymers that contain cationic groupings and anionic groupings in the macromolecule. The cationic groupings contained in the macromolecule are quaternary ammonium groups. A positively charged nitrogen atom in these quaternary ammonium groups carries four organic radicals. The anionic groupings are —COO$^-$ groups or —SO$_3^-$ groups.

The cationic polymers can be homopolymers or copolymers or polymers based on natural polymers, wherein the quaternary nitrogen groups are contained either in the polymer chain or preferably as a substituent of one or multiple monomers. The ammonium groups containing monomers can be copolymerized with non-cationic monomers. Suitable cationic monomers are unsaturated radical polymerizable compounds which carry at least one cationic group, particularly ammonium-substituted vinyl monomers, such as trialkylmethacryloxyalkylammonium, trialkylacryloxyalkylammonium, dialkyl diallyl ammonium and quaternary vinyl ammonium monomers with cyclic groups containing cationic nitrogens, such as pyridinium, imidazolium or quaternary pyrrolidones, e.g. alkylvinylimidazolium, alkylvinylpyridinium, or alkylvinylpyrrolidone salts. The alkyl groups of these monomers are preferably lower alkyl groups, such as C1- to C7-alkyl groups, with particular preference being given to C1- to C3-alkyl groups.

The ammonium groups containing monomers can be copolymerized with non-cationic monomers. Suitable co-monomers are, for example, acrylamide, methacrylamide; alkyl- and dialkylacrylamide, alkyl- and dialkylmethacrylamide, alkyl acrylate, alkylmethacrylate, vinyl caprolactone, vinyl caprolactam, vinyl pyrrolidone, vinyl esters, for example vinyl acetate, vinyl alcohol, propylene glycol or ethylene glycol, wherein the alkyl groups of these monomers preferably contain C1- to C7-alkyl groups, particularly preferably C1- to C3-alkyl groups.

Preferred cationic and zwitterionic polymers which have been found to be particularly effective components of the active ingredient combination of the present disclosure are selected from the group of copolymers of dimethyl-diallyl ammonium salts and acrylic acid, e.g. polyquaternium-22, copolymers of dimethyl-diallyl ammonium salts and methacrylic acid, copolymers of N,N,N-trimethyl-3-[(2-methyl-1-oxo-2-propen-1-yl)amino]-1-propanaminium salts and acrylic acid, copolymers of N,N,N-trimethyl-3-[(2-methyl-1-oxo-2-propen-1-yl)amino]-1-propanaminium salts and methacrylic acid, copolymers of N,N,N-trimethyl-2-[(2-methyl-1-oxo-2-propen-1-yl)amino]-1-ethanaminium salts and acrylic acid, copolymers of N,N,N-trimethyl-2-[(2-methyl-1-oxo-2-propen-1-yl)amino]-1-ethanaminium salts and methacrylic acid, copolymers of N,N,N-trimethyl-3-[(2-methyl-1-oxo-2-propen-1-yl)amino]-1-propanaminium salts, acrylic acid and acrylamide, such as polyquaternium-53 copolymers of N,N,N-trimethyl-3-[(2-methyl-1-oxo-2-propen-1-yl)amino]-1-propanaminium salts, methacrylic acid and acrylamide, copolymers of 1-ethenyl-3-methyl-1H-imidazolium salts, 1-ethenyl-1H-imidazol, 1-ethenyl-2-pyrrolidinon and methacrylic acid, e.g. polyquaternium-86, copolymers of 1-ethenyl-3-methyl-1H-imidazolium salts, 1-ethenyl-1H-imidazol, 1-ethenyl-2-pyrrolidinon and acrylic acid, copolymers containing at least one anionic structural unit of the formula (II) and at least one cationic structural unit of the formula (V)

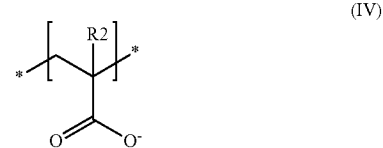

(IV)

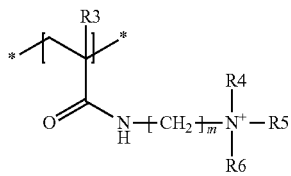

(V)

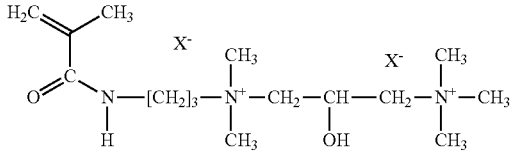

(Ia)

wherein R2 and R3 denote a hydrogen atom or a methyl group independent of each other, m denotes an integer from 2 to 6, preferably the integers 2 or 3, and the radicals R4, R5 and R6 denote $C_1$-$C_6$-alkyl group independent of each other, preferably a methyl group or propyl group independent of each other, wherein a particularly preferred zwitterionic polymer of this type was produced according to DE3929973A1, Production example 1, is known under the INCI name acrylamidopropyltrimonium chloride / acrylate copolymer;

polymer dimethyldiallylammonium salts and copolymers thereof with esters and amides of acrylic acid and methacrylic acid. Particularly preferred polymers of this type are dimethyldiallylammonium chloride-acrylamide-copolymers, in particular, having the INCI designation polyquaternium-7. Polyquaternium-7 is, for example available as a commercially available product, Merquat® 550. Another preferred polymer of this type is the homopolymer poly(dimethyldiallylammonium chloride), particularly the homopolymers with the INCI designation polyquaternium-6. Polyquaternium-6 is, for example available as a commercially available product, Merquat® 100. Additional preferred polymers of this type are terpolymers of dimethyldiallylammonium chloride-acrylamide and ammonium acrylate, in particular, having the INCI designation polyquaternium-39. Polyquaternium-39 is, for example, commercially available under the names Merquat® 3330 and Merquat® 3331. Additional preferred polymers of this type are copolymers of dimethyldiallylammonium chloride and acrylic acid, in particular, having the INCI designation polyquaternium-22. Polyquaternium-22 is, for example available as a commercially available product, Merquat® 280;

Homopolymers of the general formula -{$CH_2$-[$CR^1COO$—$(CH_2)_mN^+R^2R^3R^4$]}$_n$  $X^-$, wherein $R_1$=—H or —$CH_3$, $R^2$, $R^3$ and $R^4$ are selected independently of each other from C1-4-alkyl-, C1-4-alkenyl- or C1-4-hydroxyalkyl groups, m=1, 2, 3 or 4, n denotes a natural number and $X^-$ denotes a physiologically compatible organic or inorganic anion. As contemplated herein, in the context of these polymers, preference is given to polymers for which at least one of the following conditions applies: le denotes a methyl group, $R^2$, $R^3$ and $R^4$ denote methyl groups, m has the value 2. Halide ions, sulfate ions, phosphate ions, methosulfate ions and organic ions such as lactate, citrate, tartrate and acetate ions, for example, are suitable as physiologically compatible counterions $X^{31}$. Preference is given to methosulfates and halogenide ions, particularly chloride.

Additional preferred suitable cationic polymers which are derived from synthetic polymers are, for example, copolymers of A) from about 0.1 to about 50%, preferably from about 10 to about 50% (relative to the total number of monomers in the copolymer) monomers of Formula (Ia)

wherein X denotes chloride, sulfate, methosulfate and

A2) monomers from the group of acrylic acid, methacrylic acid and alkali metal- and ammonium salts of these acids, wherein monomer A2 comprises from about 50 to about 99.9%, preferably from about 50 to about 90% (relative to the total number of monomers in the copolymer) of the copolymer.

A most preferred polymer having the same structure as illustrated above, is commercially available under the INCI designation Polyquaternium-74.

A particularly suitable homopolymer is the optionally crosslinked poly(methacryloyloxyethyltrimethylammonium chloride) with the INCI designation Polyquaternium-37.

Other preferred agents of the present disclosure or agents used as contemplated herein are exemplified in that they contain at least one polymer selected from cationic and zwitterionic polymers in a total amount of from about 0.1-about 2 wt. %, preferably from about 0.2-about 1.5 wt. %, particularly from about 0.4-about 1 wt. %, relative to the weight of the agent in each case.

Other particularly preferred agents of the present disclosure or agents used as contemplated herein are exemplified in that they contain at least one cationic or zwitterionic polymer selected from acrylamidopropyltrimonium chloride/acrylate polymers and Polyquaternium-6, as well as mixtures thereof, in a total amount of from about 0.1-about 2 wt. %, preferably from about 0.2-about 1.5 wt. %, particularly from about 0.4-about 1 wt. %, relative to the weight of the agent in each case.

As contemplated herein, it can be preferable that the agents of the present disclosure contain sodium polyacrylate. As contemplated herein, sodium polyacrylate preferably comprises polymers with the CAS number 9003-04-7. Sodium polyacrylates preferred as contemplated herein have an average molecular weight Mw in the range from about 1,000,000 to about 20,000,000 Dalton, preferably from about 6,000,000 to about 15,000,000 Dalton. The average molecular weight $M_w$ can, for example, be determined by employing gel permeation chromatography (GPC) with polystyrene as an internal standard according to DIN 55672-3, Version 8/2007.

The mixture preferred as contemplated herein comprising sodium polyacrylate, crosslinked copolymers of acrylic acid and non-ethoxylated esters of acrylic acid having linear C10-C30-monoalcohols, branched C10-C50-alkanol and linear, saturated C8-C22-alkan-1-ol achieves a thickening of the agent with the optimal viscosity, wherein the agent also has the consistency of a gel-like cream with outstanding haptics.

Particularly preferred agents as contemplated herein contain sodium polyacrylate in a total amount of from about 0.1-about 1.5 wt. %, preferably from about 0.5-about 1.3 wt. %, particularly from about 0.8-about 1.1 wt. %, relative to the weight of the agent in each case.

In an especially preferred embodiment, the sodium polyacrylate is contained as a sodium polyacrylate pre-gelatinized in a water-in-oil emulsion. The sodium polyacrylate-containing water-in-oil emulsion preferably contains, in each case relative to its weight, from about 40-about 60 wt. % of sodium polyacrylate, from about 25-about 45 wt. % oil(s) in total, from about 0.5-about 4.9 wt. % surfactant(s) in total and from about 0.5-about 4.9 wt. % water.

The oil contained in the sodium polyacrylate-containing water-in-oil emulsion is most preferably selected from natural and synthetic hydrocarbons, most preferably from mineral oil, paraffin oils, $C_{18}$-$C_{30}$ isoparaffins, particularly isoeicosane, polyisobutenes and polydecenes, $C_8$-$C_{16}$ isoparaffins, as well as 1,3-di-(2-ethylhexyl)-cyclohexane; branched alkanols having a hydroxy group and from about 10 to about 50 carbon atoms; the benzoic acid esters of linear or branched $C_{8-22}$ alkanols; triglycerides of linear or branched, saturated or unsaturated, where necessary hydroxylated $C_{8-30}$ fatty acids, particularly natural oils; the dicarboxylic acid esters of linear or branched $C_2$-$C_{10}$ alkanols; the esters of linear or branched saturated or unsaturated fat alcohols having from about 2-about 30 carbon atoms with linear or branched saturated or unsaturated fatty acids having from about 2-about 30 carbon atoms, which can be hydroxylated; the adducts of from 1 to about 5 propylenoxide units of monovalent or multivalent $C_{8-22}$alkanols; the $C_8$-$C_{22}$ fatty alcohol esters of monovalent or multivalent $C_2$-$C_7$hydroxycarboxylic acids; the symmetrical, asymmetrical or cyclical esters of carbonic acids having $C_{3-22}$ alkanols, $C_{3-22}$ alkanediols or $C_{3-22}$ alkane triols; the esters of dimers of unsaturated $C_{12}$-$C_{22}$ fat alcohols (dimer fatty acids) having monovalent linear, branched or cyclical $C_2$-$C_{18}$ alkanols or having monovalent linear or branched $C_2$-$C_6$ alkanols; silicone oils, as well as mixtures of the aforementioned substances. The oil most preferred as contemplated herein is mineral oil.

It is especially preferred that the water-in-oil emulsion containing sodium polyacrylate contains at least one surfactant selected from nonionic surfactants. The non-ionic surfactants most preferably used are selected from, having from about 7-about 80 mol of ethylene oxide per mol, ethoxylated castor oil, ethoxylated $C_8$-$C_{24}$ alkanols having from about 5-about 30 mol ethylene oxide per mol, ethoxylated $C_8$-$C_{24}$carbonic acid having from about 5-about 30 mol of ethylene oxide per mol, having from about 4-about 50 mol of ethylene oxide per mol of sorbitan monoesters of linear saturated and unsaturated $C_{12}$-$C_{30}$ carbonic acids, which can be hydroxylated, more particularly those from myristiric acid, palmitic acid, stearic acid of mixtures of said fatty acids, alkylmono and oligoglycosides having from about 8 to about 22 carbon atoms in the alkyl radical and the ethoxylated analogs thereof, as well as mixtures of the aforementioned substances.

The ethoxylated $C_8$-$C_{24}$ alkanols have the formula $R^1O(CH_2CH_2O)_nH$, wherein $R^1$ denotes a linear or branched alkyl and/or alkenyl radical having from about 8-about 24 carbon atoms and n, the average number of ethylene oxide units per molecule, for integers from about 5-about 30, preferably from about 6-about 20, more preferably from about 6 to about 12 mol ethylene oxide to 1 mol alkanol, which is preferably selected from capryl alcohol, 2-ethylhexyl alcohol, caprin alcohol, lauryl alcohol, isotridecyl alcohol, tridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, as well as the technical mixtures thereof. Adducts from about 10-about 100 mol ethylene oxide on technical fat alcohols having from about 12-about 18 carbon atoms, such as for example coco, palm, palm kernel or sebum fat alcohols are also suitable. Trideceth-6, Isotrideceth-6, Undeceth-6, Myreth-6, Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, as well as Coceth-10, Coceth-12, Coceth-15, Coceth-20 and Coceth-30 are more preferred; Trideceth-6 and Isotrideceth-6, as well as the mixtures thereof, are most preferred.

The ethoxylated $C_8$-$C_{24}$ carbonic acids have the formula $R^1O(CH_2CH_2O)_nH$, wherein $R^1O$ denotes a linear or branched, saturated or unsaturated acyl radical having from about 8-about 24 carbon atoms and n, the average number of ethylene oxide units per molecule, for integers from about 5-about 30, preferably from about 6-about 20, more preferably from about 6 to about 12 mol ethylene oxide to 1 mol $C_8$-$C_{30}$ carbonic acid, which is preferably selected from capryl alcohol, 2-ethylhexyl alcohol, caprin alcohol, lauric acid, isotridecaric acid, myristiric acid, cetylic acid, palmitoleic acid, stearic acid, isostearic acid, oleic acid, elaidic acid, petroselic acid, arachine acid, gadoleic acid, behenic acid, erucic acid and brassidic acid, as well as the technical mixtures thereof. Adducts from about 5-about 30, preferably from about 6-about 20, more preferably from about 6 to about 12 mol of ethylene oxide on technical fatty acids having from about 12-about 18 carbon atoms, such as coco, palm, palm kernel or sebum fat alcohols are also suitable.

Agents most preferred as contemplated herein are exemplified in that they contain at least one sodium polyacrylate having an average molecular weight $M_w$ in the range from about 1,000,000 to about 20,000,000 Dalton, preferably from about 6,000,000 to about 15,000,000 Dalton, in a total quantity of from about 0.1-about 1.5 wt. %, preferably from about 0.5-about 1.3 wt. %, more preferably from about 0.8-about 1.1 wt. %, in each case relative to the total weight of the agent, wherein the sodium polyacrylate is contained pregelled in a water-in-oil emulsion, wherein said water-in-oil emulsion, in each case relative to its weight, contains from about 40-about 60 wt. % sodium polyacrylate, from about 25-about 45 wt. % oil(s) in total, preferably mineral oil, from about 0.5-about 4.9 wt. % surfactant(s) in total, preferably from about 0.5-about 4.9 wt. % nonionic surfactant(s), and from about 0.5-about 4.9 wt. % water.

As contemplated herein, preferred and preferably used agents contain, at least one oil in a total amount of from about 0.2-about 6 wt. %, preferably from about 0.5-about 5 wt. %, particularly from about 0.7-about 3 wt. %, relative to the weight of said agent in each case, wherein these quantities include the oils from the preferred sodium polyacrylate emulsion as contemplated herein. This additional oil can be selected from the same oils that can also be comprised in the sodium polyacrylate emulsions preferred as contemplated herein. The at least one additional oil contained in the sodium polyacrylate-containing water-in-oil emulsion is preferably selected from natural and synthetic hydrocarbons, most preferably from mineral oil, paraffin oils, $C_{18}$-$C_{30}$ isoparaffins, particularly isoeicosane, polyisobutenes and polydecenes, $C_8$-$C_{16}$ isoparaffins, as well as 1,3-di-(2-ethylhexyl)-cyclohexane; branched alkanols having a hydroxy group and from about 10 to about 50 carbon atoms; the benzoic acid esters of linear or branched $C_{8-22}$ alkanols; triglycerides of linear or branched, saturated or unsaturated, where necessary hydroxylated $C_{8-30}$ fatty acids, particularly natural oils; the dicarboxylic acid esters of linear or branched $C_2$-$C_{10}$ alkanols; the esters of linear or branched saturated or unsaturated fat alcohols having from about 2-about 30 carbon atoms with linear or branched saturated or unsaturated fatty acids having from about 2-about 30 carbon atoms, which can be hydroxylated; the adducts of from 1 to about 5 propylenoxide units of monovalent or multivalent $C_{8-22}$alkanols; the $C_8$-$C_{22}$ fatty alcohol esters of monovalent or multivalent $C_2$-$C_7$hydroxycarboxylic acids; the symmetrical, asymmetrical or cyclical esters of carbonic acids having $C_{3-22}$ alkanols, $C_{3-22}$ alkanediols or $C_{3-22}$ alkane triols; the esters of dimers of unsaturated $C_{12}$-$C_{22}$ fat alcohols (dimer fatty acids) having monovalent linear, branched or cyclical $C_2$-$C_{18}$ alkanols or having monovalent linear or branched $C_2$-$C_6$ alkanols; silicone oils, as well as mixtures of the aforementioned substances. As contemplated herein particular preference is given to oils selected from paraffin oils, natural oils, in particular amaranthus seed oil, apricot kernel oil, arganil, avocado oil, babassu oil, cottonseed oil, borage seed oil, cameline oil, safflower oil, peanut oil, pomegranate core oil, grapefruit seed oil, hemp oil, hazelnut oil, palm seed oil, jojoba oil, linseed oil, macadamia nut oil, corn oil, almond oil, marula oil, evening primrose oil, olive oil, palm oil, palm kernel oil, parannut oil, pecknut oil, peach kernel oil, rapeseed oil, castor oil, sandalwood oil, castor oil, sesame oil, soya oil, sunflower oil, grapeseed oil, walnut oil, wild-type oil, wheat germ oil, and the liquid fractions of coconut oil, and also synthetic triglyceride oils, in particular capric/caprylic triglycerides, furthermore the esters of linear or branched saturated or unsaturated fatty alcohols having from about 2-about 30 carbon atoms with linear or branched saturated or unsaturated fatty acids having from about 2-about 30 carbon atoms, which can be hydroxylated, in particular isopropyl palmitate and isopropyl myristate, and mixtures of the aforementioned oils.

A further essential feature of the agent as contemplated herein is the content of at least one oxidation dye precursor.

On the basis of their reaction behavior, oxidative dye precursors can be divided into two categories, so-called developer components and coupler components.

During the oxidative dyeing process, coupler components do not achieve any significant coloration by themselves. They always require the presence of developer components. Developer components can combine together to form the actual dye.

The developer and coupler components are normally used in a free form. In the case of substances with amino groups, however, use of the salt form thereof, more particularly in the form of hydrochlorides and hydrobromides or sulfates, may be preferred.

Oxidation dye precursors include oxidation dye precursors of the developer and coupler types. Particularly suitable oxidation dye precursors of the developer type are selected from at least one compound from the group of p-phenylenediamine, p-toluolenediamine, 2-(2-hydroxyethyl)-p-phenylenediamine, 2-(1,2-dihydroxyethyl)-p-phenylenediamine, N, N-bis (2-hydroxyethyl)-p-phenylenediamine, 2-methoxymethyl-p-phenylenediamine, N-(4-amino-3-methylphenyl)-N-[3-(1H-imidazol-1-yl) propyl] amine, N, N'-bis (2-hydroxyethyl)-N, N'-bis-(4-aminophenyl)-1,3-diamino-propane-2-ol, bis-(2-hydroxy-5-aminophenyl) methane, 1,3-bis (2,5-diaminophenoxy) propan-2-ol, N, N'-bis (4-aminophenyl)-1,4-diazacycloheptane, 1,10-bis (2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl) phenol, 4-amino-2-(diethylaminomethyl) phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H, 5H-pyrazolo [1,2-a] pyrazol-1-one and the physiologically tolerated salts thereof. Most preferred developer components are selected from p-toluolenediamine, 2-(2-hydroxyethyl)-p-phenylendiamine, N,N-bis-(2-hydroxyethyl)-p-phenylendiamine, 2-methoxymethyl-p-phenylendiamine and/or 4,5-diamino-1-(2-hydroxyethyl)-pyrazol and the physiologically tolerated salts and mixtures thereof.

Particularly suitable oxidation dye precursors of the coupler type are selected from the group of 3-aminophenol, 5-amino-2-methylphenol, 3-amino-2-chlor-6-methylphenol, 2-hydroxy-4-aminophenoxyethanol, 5-amino-4-chlor-2-methylphenol, 5-(2-hydroxyethyl)-amino-2-methylphenol, 2,4-dichlor-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2-hydroxyethylamino)benzol (2-amino-4-[(2-hydroxyethyl)amino]-anisol), 1,3-bis(2,4-diaminophenyl)propane, 2,6-bis(2'-hydroxyethylamino)-1-methylbenzol, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl)amino]-4,5-dimethylphenyl} amino)ethanol, 2-[3-morpholin-4-ylphenyl)amino] ethanol, 3-amino-4-(2-methoxyethoxy)-5-methylphenylamine, 1-amino-3-bis(2-hydroxyethyl)aminobenzol, resorcin, 2-methylresorcin, 4-chlorresorcin, 1,2,4-trihydroxybenzol, 2-amino-3-hydroxypyridin, 3-amino-2-methylamino-6-methoxypyridin, 2,6-dihydroxy-3,4-dimethylpyridin, 3,5-diamino-2,6-dimethoxypyridin, 1-phenyl-3-methylpyrazol-5-on, 1-naphthol, 1,5-dihydroxynaphthalin, 2,7-dihydroxynaphthalin, 1,7-dihydroxynaphthalin, 1,8-dihydroxynaphthalin, 4-hydroxyindol, 6-hydroxyindol, 7-hydroxyindol, 4-hydroxyindolin, 6-hydroxyindolin, 7-hydroxyindolin or mixtures of said compounds or the physiologically compatible salts thereof. Most preferred coupler components are selected from 3-aminophenol, 5-amino-2-methylphenol, 3-amino-2-chlor-6-methylphenol, 2-hydroxy-4-aminophenoxyethanol, 2-(2,4-diaminophenoxy)ethanol, 1-methoxy-2-amino-4-(2-hydroxyethylamino)benzol (2-Amino-4-[(2-hydroxyethyl)amino]-anisol), resorcin, 2-methylresorcin, 4-chlorresorcin, 2-amino-3-hydroxypyridin, as well as the physiologically compatible salts and mixtures thereof.

In a preferred embodiment, the dyes as contemplated herein contain one or more oxidation dye precursors in a total quantity from about 0.001 to about 5.0 wt. %, preferably from about 0.01 to about 4.0 wt. %, more preferably from about 0.2 to about 3.5 wt. %, even more preferably from about 0.3 to about 2.5 wt. % and most preferably from about 0.7 to about 1.8 wt. %, relative to the weight of the dye as contemplated herein and/or the weight of the composition used as contemplated herein (M1).

In a preferred embodiment, the dyes as contemplated herein contain one or more oxidation dye precursors, selected from at least one developer component and optionally at least one coupler component, in a total quantity from about 0.001 to about 5.0 wt. %, preferably from about 0.01 to about 4.0 wt. %, more preferably from about 0.2 to about 3.5 wt. %, even more preferably from about 0.3 to about 2.5 wt. % and most preferably from about 0.7 to about 1.8 wt. %, relative to the weight of the dye as contemplated herein and/or the weight of the composition used as contemplated herein (M1).

In a more preferred embodiment of the present disclosure, the agent as contemplated herein contains at least one partially-oxidizing dye.

In oxidative hair dyes, partially-oxidizing dyes often serve to tint unwanted red undertones, which can be produced by the melanin decomposition products, or to tint certain blond tones.

In order to obtain a balanced and subtle tint formation, the present disclosure may specify that the cosmetic agents with ODP additionally contain at least one partially-oxidizing dye.

Partially-oxidizing dyes are dyes that coat the substrate itself and do not require an oxidative process to create the color. Partially-oxidizing dyes are usually nitro-phenylendiamines, nitroaminophenols, azo dyes, anthraquinones or indophenols.

Partially-oxidizing dyes can be sub-divided into anionic, cationic and non-ionic partially-oxidizing dyes.

Preferred anionic partially-oxidizing dyes are the compounds known under the designations Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and tetrabromophenol blue.

Preferred cationic partially-oxidizing dyes are cationic triphenylmethane dyes, such as Basic Blue 7, Basic Blue 26, Basic Violet 2 and Basic Violet 14, as well as aromatic systems, which are substituted with a quaternary nitrogen group, such as Basic Yellow 57, Basic Red 76, Basic Blue 99, Basic Brown 16 and Basic Brown 17 and HC Blue 16, as well as Basic Yellow 87, Basic Orange 31 and Basic Red 51.

Preferred non-ionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzol, 2-amino-4-nitrophenol, 1,4-bis-(2-hydroxyethyl)amino-2-nitrobenzol, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzol, 1-amino-4-(2-hydroxyethyl)amino-5-chlor-2-nitrobenzol, 4-amino-3-nitrophenol, 1-(2'-Ureidoethyl)amino-4-nitrobenzol, 2-[(4-amino-2-nitrophenyl)amino]benzoic acid, 6-nitro-1,2,3,4-tetrahydrochinoxalin, 2-hydroxy-1,4-naphthoquinone, picramic acid and the salts thereof, 2-amino-6-chloro-4-nitrophenol, 4-ethylamino-3-nitrobenzoic acid and 2-chlor-6-ethylamino-4-nitrophenol.

Moreover, partially-oxidizing dyes that occur in nature, such as Henna red, Henna neutral, Henna black, chamomile blossoms sandalwood, black tea, walnut, Cascara bark, sage, logwood, madder root, catechu, ceder and alkanna root, can also be used.

The cosmetic agent according preferably contains at least one partially-oxidant in a total quantity of from about 0.001 to about 10 wt. %, preferably from about 0.01 to about 8 wt. %, more preferably from about 0.1 to about 5 wt. %, most preferably from about 0.5 to about 2 wt. %, relative to the total weight of the cosmetic agent and/or of the composition used as contemplated herein (M1).

Therefore, a further subject of the present disclosure is a kit-of-parts, comprising—packaged separately from one another:

a) at least one container (C1), containing an agent for oxidative hair dyeing containing the following, in each case relative to its weight:
from about 65 -about 83 wt. % water,
at least one oxidation dye precursor,
at least one alkalizing agent,
at least one crosslinked copolymer including acrylic acid and non-ethoxylated esters of acrylic acid with linear C10-C30 monoalcohols as monomers, wherein the crosslinked copolymer is contained in a total amount of from about 0.1-about 0.8 wt. %, preferably from about 0.1-about 0.6 wt. %, particularly from about 0.2-about 0.5 wt. %, relative to the weight of the agent in each case,
at least one linear, saturated 1-alkanol with a hydroxy group and from about 8 to about 22 carbon atoms in a total amount of from about 3-about 7 wt. %, preferably from about 4-about 6 wt. %, particularly from about 4.5-about 5.5 wt. %,
in a total amount of from about 0.2-about 2 wt. %, preferably from about 0.3-about 1.5 wt. %, particularly from about 0.4-about 0.8 wt. %, at least one glyceryl fatty acid ester having the formula (I)

wherein
R1, R2 and R3 denote a hydrogen atom or a methyl group independent of each other or a grouping of Formula (II),

wherein
R4 denotes an unbranched or branched, saturated or unsaturated $C_{11}$-$C_{27}$-alkyl group,
providing that at least one and a maximum of two of the radicals, selected from R1, R2, and R3, denotes a grouping of Formula (II);
at least one linear, saturated ethoxylated 1-alkanol with from about 8 to about 22 carbon atoms in the alkyl radical and degree of ethoxylation of from about 80 to about 120 in a total amount of from about 0.1-about 2 wt. %, preferably from about 0.2-about 1.5 wt. %, particularly from about 0.4-about 1 wt. % and
at least one linear, saturated ethoxylated 1-alkanol with from about 8 to about 22 carbon atoms in the alkyl radical and degree of ethoxylation of from about 20 to about 50 , preferably from about 30-about 35, in a total amount of from about 0.1-about 2 wt. %, preferably from about 0.2 -about 1.5 wt. %, particularly from about 0.4 -about 1 wt. %,
wherein no oxidants are contained, and
b) at least one container (C2), containing an oxidant preparation (M2), which contains from about 40-about 96 wt. %, preferably from about 70-about 93 wt. %, more preferably from about 80-about 90 wt. % of water, also hydrogen peroxide in a total quantity of from about 0.5 to about 23 wt. %, preferably from about 2.5 to about 21 wt. %, more preferably from about 4 to about 20 wt. %, even more preferably from about 5 to about 18 wt. % and most preferably from about 6 to about 12 wt. %, and which has a pH value in the range from about 2.0 to about 6.5, preferably from about 2.5-about 5.5, more preferably from about 2.8 to about 5.0, in each case measured at 20° C., wherein each of the wt. % values are relative to the weight of the oxidant preparation (M2).

A further subject matter of the present disclosure is a method for oxidative hair dyeing comprising the following method steps:

i) Providing a cosmetic agent (M1) for the oxidative hair dyeing of keratinous fibers, containing
   from about 65-about 83 wt. % water,
   at least one oxidation dye precursor,
   at least one alkalizing agent,
   at least one crosslinked copolymer including acrylic acid and non-ethoxylated esters of acrylic acid with linear C10-C30 monoalcohols as monomers, wherein the crosslinked copolymer is contained in a total amount of from about 0.1-about 0.8 wt. %, preferably from about 0.1-about 0.6 wt. %, particularly from about 0.2-about 0.5 wt. %, relative to the weight of the agent in each case,
   at least one linear, saturated 1-alkanol with a hydroxy group and from about 8 to about 22 carbon atoms in a total amount of from about 3-about 7 wt. %, preferably from about 4-about 6 wt. %, particularly from about 4.5-about 5.5 wt. %,
   in a total amount of from about 0.2-about 2 wt. %, preferably from about 0.3-about 1.5 wt. %, particularly from about 0.4-about 0.8 wt. %, at least one glyceryl fatty acid ester having the formula (I)

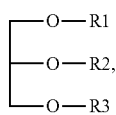

(I)

wherein
   R1, R2 and R3 denote a hydrogen atom or a methyl group independent of each other or a grouping of Formula (II),

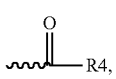

(II)

wherein
   R4 denotes an unbranched or branched, saturated or unsaturated $C_{11}$-$C_{27}$-alkyl group,
   providing that at least one and a maximum of two of the radicals, selected from R1, R2, and R3, denotes a grouping of Formula (II);
   at least one linear, saturated ethoxylated 1-alkanol with from about 8 to about 22 carbon atoms in the alkyl radical and degree of ethoxylation of from about 80 to about 120 in a total amount of from about 0.1-about 2 wt. %, preferably from about 0.2-about 1.5 wt. %, particularly from about 0.4-about 1 wt. % and
   at least one linear, saturated ethoxylated 1-alkanol with from about 8 to about 22 carbon atoms in the alkyl radical and degree of ethoxylation of from about 20 to about 50, preferably from about 30-about 35, in a total amount of from about 0.1-about 2 wt. %, preferably from about 0.2-about 1.5 wt. %, particularly from about 0.4-about 1 wt. %,
wherein no oxidants are contained, and
ii) Providing an oxidant preparation (M2), containing from about 40-about 96 wt. %, preferably from about 70-about 93 wt. %, more preferably from about 80-about 90 wt. % of water, also hydrogen peroxide in a total quantity of from about 0.5 to about 23 wt. %, preferably from about 2.5 to about 21 wt. %, more preferably from about 4 to about 20 wt. %, even more preferably from about 5 to about 18 wt. % and most preferably from about 6 to about 12 wt. %, and a pH value in the range from about 2.0 to about 6.5, preferably from about 2.5-about 5.5, most preferably from about 2.8 to about 5.0, having, in each case measured at 20° C., wherein preferably at least one surfactant, selected from anionic surfactants and nonionic surfactants, as well as mixtures thereof, in a total quantity from about 0.05-about 2 wt. %, preferably from about 0.3-about 1.5 wt. %, and at least one linear, saturatedl-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol) as well as mixtures thereof, in a total quantity from about 1-about 5 wt. %, preferably from about 1.5-about 4 wt. %, wherein optionally at least one oil in a total quantity of from about 0.2-about 50 wt. %, preferably from about 2-about 40 wt. %, more preferably from about 8-about 30 wt. %, most preferably from about 15-about 25 wt. %, and/or optionally at least one cationic surfactant, preferably in a total quantity of from about 0.05-about 3 wt. %, more preferably from about 0.1-about 1.5 wt. %, most preferably from about 0.3-about 0.9 wt. %, is contained, wherein all quantity data are relative to the weight of the oxidant preparation (M2), iii) Mixing the cosmetic agent (M1) with the oxidant preparation (M2), preferably in a weight ratio (M1):(M2) in the range from about 1:0.8 to about 1:2.5, preferably from about 1:1 to about 1:2, immediately afterwards iv) Applying the mixture obtained in Step iii) onto the hair and leaving said mixture for a period of from about 1 to about 60 minutes, preferably from about 20 to about 45 minutes at room temperature and/or at from about 30-about 60° C., v) Rinsing the hair with water and/or a cleansing composition, and vi) where necessary, applying a post-treatment agent onto the hair and, where necessary, rinsing out, then drying.

For oxidative hair dyeing, immediately before the application on the hair, the one or more oxidation dye precursors and, where applicable, one or more partially-oxidizing dyes, are usually mixed with a hydrous oxidant-containing composition (M2) to produce the ready-to-use dye and then applied to the hair. In most cases, the agent as contemplated herein (M1) and the oxidant-containing composition (M2) are matched with one another such that, at a mixing ratio of 1 to 1, relative to the parts by weight, the ready-to-use application mixture has an initial concentration of hydrogen peroxide of from about 0.5-about 12 wt. %, preferably from about 2-about 10 wt. %, more preferably from about 3-about 6 wt. % of hydrogen peroxide (calculated as 100% $H_2O_2$), in each case relative to the weight of the application mixture. However, it is equally possible for the agent as contemplated herein (M1) and the oxidant-containing composition (M2) to be matched to one another such that the concentrations required in the ready-to-use oxidant dye (application mixture) is achieved through mixture ratios other than 1:1, for example through a weight-based mixture ratio of 1:2 or 1:3 or even 2:3.

Weight-based mixture ratios preferred as contemplated herein (M1):(M2) are within the range from about 1:0.8 to about 1:2.5, more preferably within the range of from about 1:1 to about 1:2.

As contemplated herein, the expression "room temperature" describes the temperature inside the room in which a person would usually use a hair dye, i.e. usually a bathroom or a hairdressing salon, in which a temperature within the range of 10-29° C. prevails.

The leaving of the hair dyeing application mixture in method step iv) in the hair dyeing method as contemplated herein or preferred as contemplated herein can also occur at a minimum of about 30° C., preferably at from about 30-about 60° C., more preferably at from about 32-about 50° C., if the hair is heated by employing a heating hood or a heat radiator, for example.

The oxidant preparation (M2) used in the dye kit as contemplated herein and preferred as contemplated herein, as well as in the dyeing method as contemplated herein and preferred as contemplated herein contains, in each case relative to the weight thereof, from about 40-about 96 wt. %, preferably from about 70-about 93 wt. %, most preferably from about 80-about 90 wt. % of water.

The oxidant preparation (M2) used in the dye kit as contemplated herein and preferred as contemplated herein, as well as in the dyeing method as contemplated herein and preferred as contemplated herein contains, in each case relative to the weight thereof, from about 0.5 to about 23 wt. %, preferably from about 2.5 to about 21 wt. %, more preferably from about 4 to about 20 wt. %, even more preferably from about 5 to about 18 wt. and most preferably from about 6 to about 12 wt. % hydrogen peroxide.

To stabilize the hydrogen peroxide, the oxidant preparation (M2) has a pH value in the range from about 2.0 to about 6.5, preferably from about 2.5-about 5.5, most preferably from about 2.8 to about 5.0, in each case measured at 20° C.

The oxidation preparation (M2) used in further dyeing kits preferred as contemplated herein and dyeing methods preferred as contemplated herein contains at least one surfactant, selected from anionic surfactants and nonionic surfactants, as well as mixtures thereof, in a total amount of from about 0.05-about 2 wt. %, preferably from about 0.3-about 1.5 wt. %, and at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total amount of from about 1-about 5 wt. %, preferably from about 1.5-about 4 wt. %, wherein all specified quantities are relative to the weight of the oxidant preparation (M2).

The nonionic surfactants used in the oxidant preparations (M2) as contemplated herein are selected from the same surfactants from which the sodium polyacrylate emulsions used as contemplated herein contain nonionic surfactants, as indicated above.

Within the context of the present application, the aforementioned linear, saturated 1-alkanols having a hydroxy group and glyceryl fatty acid esters having the formula (i) in relation to the oxidant preparations (M2) are not counted among the surfactants.

The ethoxylated fatty alcohols that are obligatory for the agents (M1) as contemplated herein are also suitable nonionic surfactants (M2).

Anionic surfactants suitable for the oxidant preparations (M2) as contemplated herein are all anionic surfactants, suitable for use on the human body, which have an ionic group that renders them water-soluble, for example a sulfate, sulfonate or phosphate group, and a lipophilic alkyl group with approx. 8 to 30 carbon atoms, preferably from about 8 to about 24 carbon atoms in the molecule. Furthermore, the molecule can contain glycol or polyglycol ether groups, ester, ether and amide groups, as well as hydroxyl groups. Examples of suitable anionic surfactants, each in the form of the sodium, potassium and ammonium, as well as the mono-, di- and trialkanolammonium salts having from about 2 to about 4 carbon atoms in the alkanol group, polyethoxylated ether carboxylic acids, acylsarcosides, acyltaurides, acylisethionates, sulfosuccinic acid mono- and dialkyl esters and sulfosuccinic acid mono-alkylpolyoxyethylester having from 1 to about 6 ethylene oxide groups, linear alkansulfonates, linear alpha-olefinsulfonates, sulfonates of unsaturated fatty acids having up to about 6 double bonds, linear and branched fatty acid with from about 8 to about 30 carbon atoms and salts thereof, alpha-sulfo fatty acid methylesters of fatty acids, $C_8$-$C_{20}$ alkylsulfates and $C_8$-$C_{20}$ alkylether sulfates having from about 1 to about 15 oxyethyl groups, mixed surfactant hydroxysulfonates, sulfated hydroxyalkylpolyethylene and/or hydroxyalkylenpropylene glycol ethers, esters of tartaric acid or citric with ethoxylated or propoxylated fat alcohols, where necessary polyethoxylated alkyl- and/or alkenyletherphosphates, sulfated fatty acid alkylenglycol esters, as well as monoglyceridsulfates and monoglyceridethersulfates. Preferred anionic surfactants are selected from $C_8$-$C_{20}$ alkylsulfates, $C_8$-$C_{20}$alkylethersulfates and $C_8$-$C_{20}$ ether carboxylic acids, each having from about 8 to about 20 carbon atoms in the alkyl group and from 0 to about 12 ethylenoxide groups in the molecule. Particular preference is given to sodium laureth(2)sulfate, sodium cetearyl sulfate and mixtures thereof.

In a more preferred embodiment of the present disclosure, the oxidant preparation used as contemplated herein (M2) contains at least one oil in a total amount of from about 0.2-about 50 wt. %, preferably from about 2-about 40 wt. %, more preferably from about 8-about 30 wt. %, most preferably from about 15-about 25 wt. %, in each case relative to the weight of the oxidant preparation (M2).

The at least one oil contained in the oxidant preparation (M2) in a total amount of from about 0.2-about 50 wt. %, preferably from about 2-about 40 wt. %, more preferably from about 8-about 30 wt. %, particularly from about 15-about 25 wt. %, relative to the weight of the preparation (M2) in each case, is preferably selected from natural and synthetic hydrocarbons, most preferably from mineral oil, paraffin oils, $C_{18}$-$C_{30}$ isoparaffins, particularly isoeicosane, polyisobutenes and polydecenes, $C_8$-$C_{16}$ isoparaffins, as well as 1,3-di-(2-ethylhexyl)-cyclohexane; the benzoic acid esters of linear or branched $C_{8-22}$ alkanols; triglycerides of linear or branched, saturated or unsaturated, where necessary hydroxylated $C_{8-30}$ fatty acids, particularly natural oils; the dicarboxylic acid esters of linear or branched $C_2$-$C_{10}$ alkanols; the esters of linear or branched saturated or unsaturated fat alcohols having from about 2-about 30 carbon atoms with linear or branched saturated or unsaturated fatty acids having from about 2-about 30 carbon atoms, which can be hydroxylated; the adducts of from 1 to about 5 propylene oxide units of monovalent or multivalent $C_{8-22}$alkanols; the $C_8$-$C_{22}$ fatty alcohol esters of monovalent or multivalent $C_2$-$C_7$hydroxycarboxylic acids; the symmetrical, asymmetrical or cyclical esters of carbonic acids having $C_{3-22}$ alkanols, $C_{3-22}$ alkanediols or $C_{3-22}$ alkane triols; the esters of dimers of unsaturated $C_{12}$-$C_{22}$ fat alcohols (dimer fatty acids) having monovalent linear, branched or cyclical $C_2$-$C_{18}$ alkanols or having monovalent linear or branched $C_2$-$C_6$ alkanols; silicone oils, as well as mixtures of the aforementioned substances. In this context, oils particularly preferred as contemplated herein are selected from paraffin oils and the esters of linear or branched saturated or unsaturated fat alcohols having from about 2-about 30 carbon atoms with linear or branched fatty acids having from about 2-about 30 carbon atoms, which can be hydroxylated, as well as mixtures thereof, most preferred oils are selected from paraffin oil, isopropylpalmitate and isopropylmyristate, as well as mixtures thereof.

A further kit-of-parts preferred as contemplated herein and a further hair dyeing method preferred as contemplated herein are each exemplified in that the oxidant preparation (M2) contains at least one oil in a total amount of 0.2-about 50 wt. %, preferably from about 2-about 40 wt. %, preferably from about 8-about 30 wt. %, particularly from about 15-about 25 wt. % relative to the weight of the oxidant preparation (M2), and does not contain any cationic surfactants.

A further package unit (kit-of-parts) preferred as contemplated herein and a further hair dyeing method preferred as contemplated herein are exemplified in that the oxidant preparation (M2) contains at least one oil in a total amount of from about 0.2-about 50 wt. %, preferably from about 2-about 40 wt. %, more preferably from about 8-about 30 wt. %, particularly from about 15-about 25 wt. %, relative to the weight of the oxidant preparation (M2) in each case, but does not contain any polymers with a polymerization degree of at least about 200 or any polymers with a molecular weight of about 10,000 Dalton or higher.

A further package unit (kit-of-parts) preferred as contemplated herein and a further hair dyeing method preferred as contemplated herein are exemplified in that the oxidant preparation (M2) contains at least one oil in a total amount of from about 0.2-about 50 wt. %, more preferably from about 2-about 40 wt. %, even more preferably from about 8-about 30 wt. %, particularly from about 15-about 25 wt. %, relative to the weight of the oxidant preparation (M2) in each case, but does not contain any polymers with a polymerization degree of at least about 200 or any polymers with a molecular weight of about 10,000 Dalton or higher.

Cationic Surfactant in the Oxidant Preparation (M2)

The viscosity of the agent preferred as contemplated herein (M1) in the range of from about 20,000-about 90,000 mPas, preferably from about 25,000-about 65,000 mPas, more preferably from about 30,000-about 35,000 mPas, in each case measured at 22° C. by employing a Brookfield rotational viscometer at a rotational frequency of 4 rpm with Spindle TC, is ideally suited to handle this agent per se (production, dispensing, metering to produce the mixture with the oxidant preparation). The oxidant preparation (M2) usually has a low viscosity in the range of from about 10-about 6000 mPas, preferably from about 200-about 5000 mPas, particularly from about 1000-about 4500 mPas, measured at 20° C. in each case. For application on the hair, however, the application mixture ought to have a substantially higher viscosity so that it remains on the hair for the entire exposure time (in the range of from about 5-about 60 minutes, preferably from about 30-about 45 minutes) without dripping. A distinction is drawn here as to whether the application mixture is produced by shaking the two compositions (M1) and (M2) in an application bottle, from which the application mixture is applied to the hair immediately after mixing by employing an application nozzle in the form of a bottle attachment (bottle application), or whether the application mixture is produced by stirring the two compositions (M1) and (M2) in a bowl, from which the application is mixture is applied to the hair immediately after mixing by employing a brush (brush application). The bottle application is particularly suitable for dyes that are sold in retail outlets trade with an application recommendation by the consumer itself. The brush application is particularly suitable for dyes that are produced in the hairdressing salon and applied to the consumer's hair by the hairdresser.

A preferred kit-of-parts as contemplated herein and a preferred hair dyeing method as contemplated herein are each exemplified in that the oxidation preparation (M2) contains at least one surfactant, selected from anionic surfactants and nonionic surfactants, as well as mixtures thereof, in a total quantity of from about 0.05-about 2 wt. %, preferably from about 0.3-about 1.5 wt. %, and at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, each relative to the weight of the oxidant preparation (M2).

A more preferred kit-of-parts as contemplated herein and a more preferred hair dyeing method as contemplated herein are each exemplified in that the oxidation preparation (M2) contains at least one surfactant, selected from anionic surfactants and nonionic surfactants, as well as mixtures thereof, in a total quantity of from about 0.05-about 2 wt. %, preferably from about 0.3-about 1.5 wt. %, and at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, each relative to the weight of the oxidant preparation (M2), although no polymers having a polymerization degree of at least about 200 and no polymer having a molecular weight of about 10,000 Dalton or higher.

It has been found that the thickening aided by the interaction between the copolymer in the agent as contemplated herein and the aforementioned surfactant/1-alkanol mixture in the oxidant preparation (M2) is adequate, and due to the presence of a polymer with a polymerization degree of at least about 200 or a polymer with a molecular weight of about 10000 Dalton or higher, is unable to further increase and/or even be adversely affected in terms of its application properties.

A more preferred kit-of-parts as contemplated herein and a more preferred hair dyeing method as contemplated herein are each exemplified in that the oxidation preparation (M2) contains at least one surfactant, selected from anionic surfactants and nonionic surfactants, as well as mixtures thereof, in a total quantity of from about 0.05-about 2 wt. %, preferably from about 0.3-about 1.5 wt. %, at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, and at least one oil in a total quantity of from about 0.2-about 50 wt. %, preferably from about 2-about 40 wt. %, more preferably from about 8-about 30 wt. %, most preferably from about 15-about 25 wt. %, each relative to the weight of the oxidant preparation (M2).

The application mixtures thus achieved, preferably with weight-based mixture ratios (M1):(M2) in the range of from about 1:0.8 to about 1:2.5 have a viscosity in the range of from about 10,000-about 60,000 mPas, preferably from about 15,000-about 40,000 mPas, particularly from about 20,000-about 30,000 mPas, in each case measured at 20° C. (Brookfield viscometer, at a rotational frequency of 4 rpm with Spindle No. 5).

A more preferred kit-of-parts as contemplated herein and a more preferred hair dyeing method as contemplated herein are each exemplified in that the oxidation preparation (M2) contains at least one surfactant, selected from anionic surfactants and nonionic surfactants, as well as mixtures thereof, in a total quantity of from about 0.05-about 2 wt. %, preferably from about 0.3-about 1.5 wt. %, at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, and at least one oil in a total quantity of from about 0.2-about 50 wt. %, preferably from about 2-about 40 wt. %, more preferably from about 8-about 30 wt. %, most preferably from about 15-about 25 wt. %, each relative to the weight of the oxidant preparation (M2), although no polymers having a polymerization degree of at least about 200 and no polymers having a molecular weight of about 10,000 Dalton or higher.

It was also surprisingly found an application mixture having a viscosity particularly suitable for bottle application is obtained if the agent as contemplated herein or preferred as contemplated herein (M1) is mixed with an oxidant preparation (M2) containing at least one copolymer, selected from cross-linked acrylic acid/acrylic acid-C1-C6-alkyl ester copolymers and cross-linked methacrylic acid/acrylic acid-C1-C6-alkyl ester copolymers, preferably in a total quantity from about 0.1-about 7 wt. %, more preferably from about 0.5-about 6 wt. %, most preferably from about 1-about 4.5 wt. %, in each case relative to the weight of the oxidant preparation (M2). The mixing of the agent as contemplated herein or preferred as contemplated herein with such an oxidation preparation (M2) leads to the desired viscosity increase. The medium-viscosity consistency of the application mixture thus obtained leads to optimum application properties, more particularly for the bottle application. The application mixtures thus achieved, preferably with weight-based mixture ratios (M1):(M2) in the range of from about 1:0.8 to about 1:2.5 have a viscosity in the range of from about 10,000-about 60,000 mPas, preferably from about 15,000-about 40,000 mPas, particularly from about 20,000-about 30,000 mPas, in each case measured at 20° C. (Brookfield viscometer, at a rotational frequency of 4 rpm with Spindle No. 5).

Surprisingly, it was found that an application mixture with a viscosity especially suitable for brush application is achieved if the agent as contemplated herein or preferred as contemplated herein (M1) is mixed with an oxidant preparation (M2) that contains at least one cationic surfactant. During mixing, the interaction between the at least one crosslinked copolymer of acrylic acid and non-ethoxylated esters of acrylic acid with linear C10-C30 monoalcohols and the at least one cationic surfactant leads to the desired increase in viscosity. The pasty consistency of the application mixture thus obtained leads to optimum application properties, more particularly for the brush application. The application mixtures thus achieved, preferably with weight-based mixture ratios (M1):(M2) in the range of from about 1:0.8 to about 1:2.5 have a viscosity in the range of from about 15,000-about 60,000 mPas, preferably from about 20,000-about 50,000 mPas, particularly from about 25,000-about 35,000 mPas, in each case measured at 20° C. (Brookfield viscometer, at a rotational frequency of 4 rpm with Spindle No. 5).

In a more preferred embodiment of the present disclosure, the oxidant preparation used as contemplated herein (M2) contains at least one cationic surfactant, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2).

Cationic surfactants are surfactants, i.e. surfactant compounds, each having one or more positive charges. Cationic surfactants contain exclusively positive charges. Usually, said surfactants are constructed from a hydrophobic part and a hydrophilic head group, wherein the hydrophobic part normally includes a hydrocarbon structure (e.g. including one or two linear or branched alkyl chains), and the positive charge(s) are localized in the hydrophilic head group. Cationic surfactants adsorb at boundary surfaces and aggregate in hydrous solutions above the critical micelle formation concentration to form positively charged micelles.

As contemplated herein, preferred cationic surfactants are of the type of quaternary ammonium compounds, esterquats and alkyl amidoamines. Preferred quaternary ammonium compounds are ammonium halogenides, such as alkyltrimethylammoniumchloride, dialkyldimethylammoniumchloride, trialkylmethylammoniumchloride, as well as the imidazolium compounds known under the INCI trade names of Quatemium-27 and Quatemium-83. Additional preferred quaternary ammonium compounds are tetraalkylammonium salts, particularly known under the INCI designation the quaternium-52, a poly(oxy-1,2-ethanediyl), ((octadecylnitrilo)tri-2,1-ethanediyl)tris(hydroxy)phosphate (1:1)-salt, which has the general structural formula (III), wherein $x+y+z=10$:

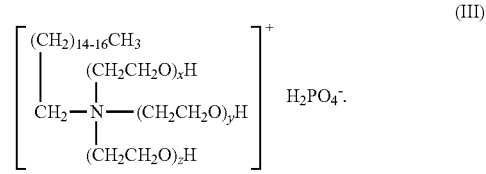

The long alkyl chains of the aforementioned surfactants preferably have from about 10 to about 22, more preferably from about 12 to about 18 carbon atoms. Particularly preferred are behenyl trimethyl ammonium chloride, stearyl trimethyl ammonium chloride and cetyl trimethyl ammonium chloride, wherein stearyl trimethyl ammonium chloride is most preferred. Other suitable cationic surfactants as contemplated herein are quaternary protein hydrolysates. Alkylamidoamines are usually produced through the amidation of natural or synthetic fatty acids and fatty acid molecules with dialkylaminoamines. As contemplated herein, Tegoamid® S 18 (stearamidopropyldimethylamin) is a suitable compound from this substance group. Esterquats are substances containing both at least one ester function and at least quaternary ammonium group as the structural element. Preferred esterquats are quaternated ester salts of fatty acids with triethanolamine, quaternated ester salts of fatty acids with diethanolalkyl amines and quaternated ester salts of fatty acids with 1,2-dihydroxypropyldialkylamines. Such products are sold under the trade names of Stepantex, Dehyquart and Armocare.

With respect to optimum application properties and optimum dye results, C10-C22 alkyl trimethyl ammonium chloride has proved to be particularly suitable. Particularly preferred oxidant preparations used as contemplated herein (M2) are therefore exemplified in that they contain at least one cationic surfactant in a total amount of from about 0.05-about 3 wt. %, preferably from about 0.1-about 1.5 wt. %, particularly from about 0.3-about 0.9 wt. %, in each case relative to the weight of the oxidant preparation (M2), wherein preferably at least one surfactant, selected from C10-C22 alkyl trimethyl ammonium chlorides, most preferably selected from behenyl trimethyl ammonium chloride, stearyl trimethyl ammonium chloride and cetyl trimethyl ammonium chloride, as well as mixtures of said surfactants, is contained. Particularly preferred oxidant preparations (M2) used as contemplated herein contain stearyltrimethylammonium chloride in a total amount of from about 0.05-about 3 wt. %, preferably from about 0.1-about 1.5 wt. %, particularly from about 0.3-about 0.9 wt. %, relative to the weight of the oxidant preparation (M2) in each case.

A further kit-of-parts preferred as contemplated herein and a further hair dyeing method preferred as contemplated herein are each exemplified in that the oxidant preparation (M2) contains at least one cationic surfactant in a total amount of from about 0.05-about 3 wt. %, preferably from about 0.1-about 1.5 wt. %, particularly from about 0.3-about 0.9 wt. % relative to the weight of the oxidant preparation (M2).

A further kit-of-parts preferred as contemplated herein and a further hair dyeing method preferred as contemplated herein are exemplified in that the oxidant preparation (M2) contains at least one cationic surfactant, preferably in a total amount of from about 0.05-about 3 wt. %, more preferably from about 0.1-about 1.5 wt. %, most preferably from about 0.3-about 0.9 wt. %, in each case relative to the weight of the oxidant preparation (M2), but contains no polymer with a polymerization degree of at least about 200 and no polymer with a molecular weight of about 10,000 Dalton or higher.

It was found that the thickening aided by the interaction between the copolymer in the agent as contemplated herein and the cationic surfactant in the oxidant preparation (M2) is adequate, and due to the presence of a polymer with a polymerization degree of at least about 200 or a polymer with a molecular weight of about 10,000 Dalton or higher, is unable to further increase and/or even be adversely affected in terms of its application properties.

A further kit-of-parts preferred as contemplated herein is exemplified in that the oxidant preparation (M2) contains at least one copolymer, selected from cross-linked acrylic acid/acrylic acid-C1-C6 alkyl ester-copolymers and cross-linked methacrylic acid/acrylic acid-C1-C6-alkyl ester copolymers, preferably in a total quantity of from about 0.1-about 7 wt. %, more preferably from about 0.5-about 6 wt. %, most preferably from about 1-about 4.5 wt. %, in each case relative to the weight of the oxidant preparation (M2), and preferably contains no cationic surfactant.

A further method for oxidative hair dyeing as contemplated herein is exemplified in that the oxidant preparation (M2) contains at least one copolymer, selected from cross-linked acrylic acid/acrylic acid-C1-C6 alkyl ester-copolymers and cross-linked methacrylic acid/acrylic acid-C1-C6-alkyl ester copolymers, preferably in a total quantity of from about 0.1-about 7 wt. %, more preferably from about 0.5-about 6 wt. %, most preferably from about 1-about 4.5 wt. %, in each case relative to the weight of the oxidant preparation (M2), and preferably contains no cationic surfactant.

Preferred cross-linked copolymers of this type are selected from—in each case cross-linked—methacrylic acid/methylacrylate-, methacrylic acid/ethylacrylate-, methacrylic acid/propylacrylate-, methacrylic acid/butylacrylate-, methacrylic acid/pentylacrylate-, methacrylic acid/hexylacrylate-, acrylic acid/methylacrylate-, acrylic acid/ethylacrylate-, acrylic acid/propylacrylate-, acrylic acid/butylacrylate-, acrylic acid/pentylacrylate- and acrylic acid/hexylacrylate copolymers and the mixtures thereof.

A further package unit preferred as contemplated herein is exemplified in that the oxidant preparation (M2) contains at least one cross-linked copolymer, selected from—in each case cross-linked—methacrylic acid/methylacrylate-, methacrylic acid/ethylacrylate-, methacrylic acid/propylacrylate-, methacrylic acid/butyl acrylate-, methacrylic acid/pentylacrylate-, methacrylic acid/hexylacrylate-, acrylic acid/methyl acrylate-, acrylic acid/ethyl acrylate-, acrylic acid/propylacrylate-, acrylic acid/butylacrylate, acrylic acid/pentyl acrylate- and acrylic acid/hexylacrylate-copolymers and mixtures thereof, in a total quantity from about 0.1-about 7 wt. %, preferably from about 0.5-about 6 wt. %, most preferably from about 1-about 4.5 wt. %, in each case relative to the weight of the oxidant preparation (M2), and no cationic surfactants.

A further preferred method for oxidative hair coloring as contemplated herein is exemplified in that the oxidant preparation (M2) contains at least one crosslinked copolymer selected from—crosslinked in each case—methacrylic acid/methacrylate-, methacrylic acid/ethylacrylate-, methacrylic acid/propylacrylate-, methacrylic acid//butylacrylate-, methacrylic acid/pentylacrylate-, methacrylic acid//hexylacrylate-, acrylic acid/methylacrylate-, acrylic acid/ethylacrylate-, acrylic acid/propylacrylate-, acrylic acid// butylacrylate-, acrylic acid/pentylacrylate- and acrylic acid/ hexylacrylate-copolymers and mixtures thereof, in a total amount of from about 0.1-about 7 wt. %, more preferably from about 0.5-about 6 wt. %, particularly from about 1-about 4.5 wt. %, relative to the weight of the oxidant preparation (M2) in each case, and preferably containing no cationic surfactants.

Moreover, the oxidant preparations as contemplated herein and preferred as contemplated herein (M2) can contain stabilizers, more particularly complexing agents, and pH buffer substances.

With respect to the cosmetic agent (M1) in container C1 and the oxidant preparation (M2) in container C2 of the kit as contemplated herein and preferred as contemplated herein, the statements made about the agents as contemplated herein and preferred as contemplated herein apply mutatis mutandis.

With respect to the cosmetic agent (M1) in container C1 and the method for oxidative hair dyeing as contemplated herein and preferred as contemplated herein, the statements made about the agents as contemplated herein and preferred as contemplated herein apply mutatis mutandis.

With respect to oxidant preparation (M2) in container C1 and the method for oxidative hair dyeing as contemplated herein and preferred as contemplated herein, the statements made about the oxidant preparations (M2) of the kits as contemplated herein and preferred as contemplated herein apply mutatis mutandis.

The container wall of container C1 and C2 is preferably made of a polyolefin, such as polypropylene (PP), high density polyethylene (HDPE), medium density polyethylene (MDPE), low density polyethylene (LDPE), linear low density polyethylene (LLDPE). Polyethylene is particularly suitable, in particular high-density polyethylene (HDPE). For improved intermixing of (M1) and (M2), it is preferred that the container (C2) containing the oxidant preparation (M2) is designed as a bottle and has a re-closable opening, such as, a snap-action or screw-type closure. This enables easier addition of color-changing agent from container (C1), which is preferably designed as a bottle made of a polyolefin.

The following examples are intended to explain the subject matter of the present disclosure without having any limiting effect.

TABLE 1

Dye creams for oxidative hair dyeing (all specified quantities in wt. %)

| Ingredient | Comparison 1 | Comparison 2 | E1 | E2 | E3 | E4 | Comparison 3 |
|---|---|---|---|---|---|---|---|
| Cetyl alcohol | 3.60 | 3.60 | 3.60 | 3.60 | 3.60 | 3.24 | 3.24 |
| Stearyl alcohol | 2.00 | 2.00 | 2.00 | 2.00 | 2.00 | 1.80 | 1.80 |
| Paraffin oil | 2.10 | 2.10 | 2.10 | 2.10 | 2.10 | 1.89 | 1.89 |
| Ceteareth-30 | 1.20 | 1.20 | 1.20 | 1.20 | 1.20 | 1.08 | 1.08 |
| Steareth-100 | 0.60 | 0.60 | 0.60 | 0.60 | 0.60 | 0.54 | 0.54 |
| Glyceryl stearate (1:1 mixture of glyceryl monostearate and glyceryl distearate) | 0.60 | 0.60 | 0.60 | 0.60 | 0.60 | 0.54 | 0.54 |
| 1,2-Propanediol | 6.00 | 6.00 | 6.00 | 6.00 | 6.00 | 5.40 | 5.40 |
| Acrylamide propyltrimonium chloride/acrylate copolymer* | 0.80 | 0.80 | 0.80 | 0.80 | 0.80 | 0.80 | 0.80 |
| Ammonium hydroxide | 2.50 | 2.50 | 2.50 | 2.50 | 2.50 | 2.50 | 2.50 |
| Acrylates/C10-30 Alkyl Acrylate Crosspolymer | — | 0.05 | 0.10 | 0.20 | 0.50 | 0.50 | — |
| Toluene-2,5-diaminsulfate | 4.00 | 4.00 | 4.00 | 4.00 | 4.00 | 4.00 | 4.00 |
| Resorcin | 2.00 | 2.00 | 2.00 | 2.00 | 2.00 | 2.00 | 2.00 |
| Water | 74.60 | 74.55 | 74.50 | 74.40 | 74.10 | 75.71 | 76.21 |
| Viscosity [mPas]** | 32,000 | 32,500 | 58,500 | 61,500 | 85,250 | 33,500 | not producible/phase separation |

*zwitterionic polymer according to DE3929973A1, Production example 1
**viscosity: measured at 22° C. in each case with a Brookfield rotation viscosimeter, rotation frequency 4 rpm, spindle TC The comparison of the two comparison compositions V1 and V2 demonstrates that an addition of 0.05 wt. % acrylates/C10-30 alkyl acrylate crosspolymer does not have a discernible influence on the viscosity of the cream. By contrast, addition of an amount of acrylates/C10-30 alkyl acrylate crosspolymer as contemplated herein nearly doubles the viscosity (viscosity increase by 1.8 times).

The addition of 0.5 wt. % acrylates/C10-30 alkyl acrylate crosspolymer (cf. E4 and V1) makes it possible to reduce the amount of grease phase by 10 wt. % without negatively influencing the viscosity. The reduction of the amount of grease phase by 10 wt. % alone, without addition of acrylates/C10-30 alkyl acrylate crosspolymer results in a total loss of the emulsion stability (cf. V3 and VI).

TABLE 2

Developers containing oxidant for the color cream from Table 1

| Ingredient | Test sample (wt. %) |
|---|---|
| Sodium benzoate | 0.04 |
| Dipicolinic acid (2,6-dicarboxypyridin) | 0.10 |
| Di-sodium pyrophosphate | 0.10 |
| Potassium hydroxide | 0.10 |
| 1,2-Propanediol | 0.50 |
| Etidronic acid | 0.15 |
| Paraffin oil | 2.00 |
| Cetearyl alcohol | 3.40 |
| Ceteareth-20 | 1.00 |
| Hydrogen peroxide | 6.00 |
| Water | ad 100.00 |

Viscosity: 3500 mPas, measured at 20° C. with a rotation viscosimeter (Haake VT 550) with a rotation frequency of 4 rpm with measurement geometry MV II

TABLE 3

Developers containing oxidant for the color cream from Table 1

| Ingredient | Test sample (wt. %) |
|---|---|
| Sodium benzoate | 0.04 |
| Dipicolinic acid (2,6-dicarboxypyridin) | 0.10 |
| Di-sodium pyrophosphate | 0.10 |
| Potassium hydroxide | 0.10 |
| 1,2-Propanediol | 1.00 |

TABLE 3-continued

Developers containing oxidant for the color cream from Table 1

| Ingredient | Test sample (wt. %) |
|---|---|
| Etidronic acid | 0.15 |
| Paraffin oil | 0.30 |
| Stearyl trimethyl ammonium chloride | 0.30 |
| Cetearyl alcohol | 3.40 |
| Ceteareth-20 | 1.00 |
| Hydrogen peroxide | 6.00 |
| Water | ad 100.00 |

Viscosity: 4500 mPas, measured at 20° C. with a rotation viscosimeter (Haake VT 550) with a rotation frequency of 4 rpm with measurement geometry MV II

TABLE 4

Developers containing oxidant for the color cream from Table 1

| Ingredient | Test sample (wt. %) |
|---|---|
| Sodium hydroxide | 0.40 |
| Dipicolinic acid (2,6-dicarboxypyridin) | 0.10 |
| Di-sodium pyrophosphate | 0.03 |
| Etidronic acid | 0.15 |
| Mixture of crosslinked (meth)acrylic acid/ acrylic acid -C1-C6-alkyl ester copolymers(e.g. Aculyn 33A) | 4.20 (active) |
| Sodium laureth(2)sulphate | 0.50 |
| Hydrogen peroxide | 6.00 |
| Water | ad 100.00 |

* Aculyn 33A: hydrous dispersion of Acrylates Copolymer (mixture of cross-linked (meth)acrylic acid/acrylic acid -C1-C6-alkyl ester copolymers); 28 wt. % polymer content (active substance)

Viscosity: 200 mPas, measured at 20° C. by employing a Brookfield rotational viscometer at a rotational frequency of 20 rpm with Spindle 2

TABLE 5

Developers containing oxidant for the color cream from Table 1

| Ingredient | Test sample (wt. %) |
|---|---|
| Sodium benzoate | 0.04 |
| Dipicolinic acid (2,6-dicarboxypyridin) | 0.10 |
| Di-sodium pyrophosphate | 0.10 |
| Potassium hydroxide | 0.12 |
| Etidronic acid | 0.15 |
| Paraffin oil | 20.00 |
| Sodium cetearyl sulfate | 0.36 |
| Cetearyl alcohol | 3.50 |
| PEG-40 Castor Oil | 0.70 |
| Hydrogen peroxide | 6.00 |
| Water | ad 100.00 |

Viscosity: 7500 mPas, measured at 20° C. with a rotation viscosimeter (Haake VT 550) with a rotation frequency of 4 rpm with measurement geometry MV II

TABLE 6

Developers containing oxidant for the color cream from Table 1

| Ingredient | Test sample (wt. %) |
|---|---|
| Sodium benzoate | 0.04 |
| Di-sodium pyrophosphate | 0.10 |
| Potassium hydroxide | 0.12 |
| Etidronic acid | 0.15 |
| Sodium cetearyl sulfate | 0.20 |
| Cetearyl alcohol | 1.70 |
| PEG-40 Castor Oil | 0.40 |

TABLE 6-continued

Developers containing oxidant for the color cream from Table 1

| Ingredient | Test sample (wt. %) |
|---|---|
| Hydrogen peroxide | 6.00 |
| Water | ad 100.00 |

Viscosity: 2500 mPas, measured at 20° C. with a rotation viscosimeter (Haake VT 550) with a rotation frequency of 4 rpm with measurement geometry MV II Production of the Application Mixtures and Coloration on Hair Dye gel and developer according to Table 7 were mixed with one another in a homogeneous manner. The application mixtures thus obtained were applied, immediately after production, to human hair (natural white hair, Kerling) (liquor ratio 4 gram application mixture per gram of hair and left on the hair for 30 minutes at room temperature (22° C.). The strands were then rinsed out and towel-dried.

TABLE 7

Production of the application mixtures for coloration on hair

| Alkaline dye cream (M1) | Developer (M2) | Weight ratio (M1):(M2) | Viscosity of the application mixture [mPas]** |
|---|---|---|---|
| according to Table 1 | according to Table 2 | 1:2 | 22,500 |
| according to Table 1 | according to Table 2 | 1:1 | 24,000 |

**measured at 20° C. by employing a Brookfield rotational viscometer at a rotational frequency of 4 rpm with Spindle 5.

The invention claimed is:

1. Agent for oxidative hair dyeing comprising, relative to the weight of the agent, from about 65 to about 83 wt. % water, at least one oxidation dye precursor, at least one alkalizing agent, at least one crosslinked copolymer comprising acrylic acid and non-ethoxylated esters of acrylic acid with linear C10-C30-monoalcohols as monomers, wherein the crosslinked copolymer is included in a total amount of from about 0.1 to about 0.8 wt. %, at least one linear, saturated 1-alkanol with a hydroxy group and from about 8 to about 22 carbon atoms in a total amount of from about 3 to about 7 wt. %, in a total amount of from about 0.2 to about 2 wt. %, at least one glyceryl fatty acid ester having the formula (I)

(I)

wherein

R1, R2 and R3 denote a hydrogen atom or a methyl group independent of each other or a grouping of Formula (II),

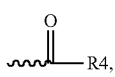

(II)

wherein
R4 denotes an unbranched or branched, saturated or unsaturated C11-C27-alkyl group,
providing that at least one and a maximum of two of the radicals, selected from R1, R2, and R3, denotes a grouping of Formula (II);
at least one linear, saturated ethoxylated 1-alkanol with from about 8 to about 22 carbon atoms in the alkyl radical and degree of ethoxylation of from about 80 to about 120 in a total amount of from about 0.1 to about 2 wt. %, and
at least one linear, saturated ethoxylated 1-alkanol with from about 8 to about 22 carbon atoms in the alkyl radical and degree of ethoxylation of from about 20 to about 50, in a total amount of from about 0.1 to about 2 wt. %,
wherein no oxidants are included; and
wherein the agent has a viscosity of from about 30,000 to about 35,000 mPas, measured at 22° C. by employing a Brookfield rotational viscometer at a rotational frequency of 4 rpm with Spindle TC.

2. Agent according to claim 1 wherein the alkalizing agent is selected from the group of ammonium hydroxide, basic amino acids, alkalihydroxides, alkanolamines, alkali metal metasilicates, alkali phosphates and alkali hydrogen phosphates, or the mixtures thereof.

3. Agent according to claim 1 having a pH value in the range of from about 8 to about 12, measured at 20° C.

4. Agent according to claim 1 wherein the at least one crosslinked copolymer of acrylic acid and non-ethoxylated esters of the acrylic acid with linear C10-C30 mono-alcohols is selected from copolymers having the INCI designation Acrylates/C10-30 Alkyl Acrylate Crosspolymer.

5. Agent according to claim 1 further comprising at least one linear saturated alcohol with two or three hydroxy groups and from about 2 to about 8 carbon atoms in the alkyl group, is included in a total amount of from about 0.5 to about 15 wt. %.

6. Agent according to claim 1 wherein the at least one linear, saturated ethoxylated 1-alkanol with from about 8 to about 22 carbon atoms in the alkyl radical and an ethoxylation degree of from about 80 to about 120 is Steareth-100 and the at least one linear, saturated ethoxylated 1-alkanol with from about 8 to about 22 carbon atoms in the alkyl radical and an ethoxylation degree of from about 20 to about 50 is selected from Ceteth-20, Ceteth-25, Ceteth-30, Ceteth-35, Ceteth-40, Ceteth-45, Ceteth-50, Steareth-20, Steareth-25, Steareth-30, Steareth-35, Steareth-40, Steareth-45, Steareth-50, Ceteareth-20, Ceteareth-25, Ceteareth-30, Ceteareth-35, Ceteareth-40, Ceteareth-45, Ceteareth-50 and mixtures thereof.

7. Kit-of-parts comprising—packaged separately from one another—
a) at least one container (C1), comprising an agent (M1) for oxidative hair dyeing according claim 1, and
b) at least one container (C2), comprising an oxidant preparation (M2), which comprises from about 40 to about 96 wt. % of water, hydrogen peroxide in a total quantity of from about 0.5 to about 23 wt. %, and which has a pH value in the range from about 2.0 to about 6.5, measured at 20° C., wherein each of the wt. % values are relative to the weight of the oxidant preparation (M2).

8. Kit-of-parts according to claim 7 wherein the oxidation preparation (M2) further comprises at least one surfactant, selected from anionic surfactants and nonionic surfactants, or mixtures thereof, in a total amount of from about 0.05 to about 2 wt. %, and at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), or mixtures thereof, in a total amount of from about 1 to about 5 wt. %, wherein all specified quantities are relative to the weight of the oxidant preparation (M2).

9. Kit-of-parts according to claim 7, wherein the oxidant preparation (M2) comprises at least one oil in a total amount of from about 0.2 to about 50 wt. %, relative to the weight of the oxidant preparation (M2).

10. Kit-of-parts according to claim 7 wherein the oxidant preparation (M2) comprises at least one cationic surfactant.

11. Kit-of-parts according to claim 7 wherein the oxidant preparation (M2) comprises no polymer with a polymerization degree of at least about 200 and no polymer with a molecular weight of about 10,000 Dalton or higher.

12. Kit-of-parts according to claim 7 wherein the oxidant preparation (M2) does not contain any cationic surfactants.

13. Method for oxidative hair dyeing, comprising the following method steps:
i) Providing a cosmetic agent (M1) for oxidative hair dyeing according to claim 1,
ii) Providing an oxidant preparation (M2), comprising from about 40 to about 96 wt. %, of water, hydrogen peroxide in a total quantity of from about 0.5 to about 23 wt. %, and a pH value in the range from about 2.0 to about 6.5, measured at 20° C., at least one surfactant, selected from anionic surfactants and nonionic surfactants, or mixtures thereof, in a total quantity from about 0.05 to about 2 wt. %, and at least one linear, saturated 1-alkanol having from about 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol) or mixtures thereof, in a total quantity from about 1 to about 5 wt. %, optionally at least one oil in a total quantity of from about 0.2 to about 50 wt. %, and/or optionally at least one cationic surfactant, in a total quantity of from about 0.05 to about 3 wt. %, wherein all quantity data are relative to the weight of the oxidant preparation (M2),
iii) Mixing the cosmetic agent (M1) with the oxidant preparation (M2), immediately afterwards
iv) Applying the mixture obtained in Step iii) onto the hair and leaving said mixture for a period of from about 1 to about 60 minutes at room temperature or at from about 30 to about 60° C.,
v) Rinsing the hair with water and/or a cleansing composition, and
vi) where necessary, applying a post-treatment agent onto the hair and, where necessary, rinsing out, then drying.

14. Method for oxidative hair dyeing according to claim 13 wherein the oxidant preparation (M2) comprises no polymer with a polymerization degree of at least about 200 and no polymer with a molecular weight of about 10000 Dalton or higher.

15. Agent according to claim 1, wherein at least one linear saturated alcohol with two or three hydroxy groups and from about 2 to about 8 carbon atoms in the alkyl group is selected from 1,2-propanediol, glycerin, or mixtures thereof.

16. Agent according to claim 1, having a pH value in the range of from about 9.5 to about 10.5, measured at 20° C.

17. Agent according to claim 1, wherein:
the at least one crosslinked copolymer is included in a total quantity of from about 0.2 to about 0.5 wt. %,
the at least one linear, saturated 1-alkanol with a hydroxy group and from about 8 to about 22 carbon atoms is included in a total amount of from about 4.5 to about 5.5 wt. %,
the at least one glycerol fatty acid of Formula (I) is included in a total quantity of from about 0.4 to about 0.8 wt. %,
the at least one linear, saturated ethoxylated 1-alkanol with from about 8 to about 22 carbon atoms in the alkyl radical and degree of ethoxylation of from about 80 to about 120 in a total amount of from about 0.4 to about 1 wt. %,
the at least one linear, saturated ethoxylated 1-alkanol with from about 8 to about 22 carbon atoms in the alkyl radical and degree of ethoxylation of from about 30 to about 35, in a total amount of from about 0.4 to about 1 wt. %, and
the agent has a pH value in the range of from about 8 to about 12, measured at 20° C.,
wherein all amounts are relative to weight of the agent.

18. Kit-of-parts according to claim 7, wherein the oxidant preparation (M2) comprises from about 80 to about 90 wt. % of water, hydrogen peroxide in a total quantity of from about 6 to about 12 wt. %, and has a pH value in the range from about 2.8 to about 5.0, measured at 20° C., wherein each of the wt. % values are relative to the weight of the oxidant preparation (M2).

19. Kit-of-parts according to claim 10 wherein the at least one cationic surfactant is included in a total quantity of from about 0.05 to about 3 wt. %, relative to the weight of the oxidant preparation (M2).

20. Agent for oxidative hair dyeing comprising, relative to the weight of the agent,
from about 65 to about 83 wt. % water,
at least one oxidation dye precursor,
at least one alkalizing agent,
at least one crosslinked copolymer comprising acrylic acid and non-ethoxylated esters of acrylic acid with linear C10-C30-monoalcohols as monomers, wherein the crosslinked copolymer is included in a total amount of from about 0.2 to about 0.5 wt. %,
a linear, saturated 1-alkanol chosen from cetyl alcohol, stearyl alcohol, and combinations thereof present in a total amount of from about 4.5 to about 5.5 wt. %,
in a total amount of from about 0.4 to about 0.8 wt. %, at least one glyceryl fatty acid ester having the formula (I)

wherein
R1, R2 and R3 denote a hydrogen atom or a methyl group independent of each other or a grouping of Formula (II),

wherein
R4 denotes an unbranched or branched, saturated or unsaturated $C_{11}$-$C_{27}$-alkyl group,
providing that at least one and a maximum of two of the radicals, selected from R1, R2, and R3, denotes a grouping of Formula (II);

Steareth-100 in a total amount of from about 0.4 to about 1 wt. %, and

Ceteareth-30 in a total amount of from about 0.4 to about 1 wt. %, wherein no oxidants are included; and wherein the agent has a viscosity of from about 30,000 to about 35,000 mPas, measured at 22° C. by employing a Brookfield rotational viscometer at a rotational frequency of 4 rpm with Spindle TC.

* * * * *